(12) United States Patent
Pobitschka

(10) Patent No.: US 10,350,340 B2
(45) Date of Patent: Jul. 16, 2019

(54) METHOD FOR SEPARATING BLOOD, SEPARATION CONTAINER FOR A BLOOD CENTRIFUGE, SYSTEM FOR FILLING A FREEZER CONTAINER

(76) Inventor: Walter Pobitschka, Bad Homburg (DE)

( * ) Notice: Subject to any disclaimer, the term of this patent is extended or adjusted under 35 U.S.C. 154(b) by 227 days.

(21) Appl. No.: 14/127,817

(22) PCT Filed: Jun. 19, 2012

(86) PCT No.: PCT/DE2012/000628
§ 371 (c)(1),
(2), (4) Date: May 5, 2014

(87) PCT Pub. No.: WO2017/175069
PCT Pub. Date: Dec. 27, 2012

(65) Prior Publication Data
US 2014/0234828 A1    Aug. 21, 2014

(30) Foreign Application Priority Data
Jun. 19, 2011  (DE) .................. 10 2011 105 311

(51) Int. Cl.
*A01N 1/02* (2006.01)
*A61M 1/02* (2006.01)
*A61M 1/36* (2006.01)

(52) U.S. Cl.
CPC ......... *A61M 1/0272* (2013.01); *A01N 1/0268* (2013.01); *A61M 1/0209* (2013.01); *A61M 1/3693* (2013.01); *A61M 2202/0429* (2013.01); *A61M 2202/0462* (2013.01)

(58) Field of Classification Search
None
See application file for complete search history.

(56) References Cited

U.S. PATENT DOCUMENTS

| | | | |
|---|---|---|---|
| 4,040,959 A | 8/1977 | Berman et al. | |
| 4,617,009 A | 10/1986 | Oehlin et al. | |
| 2001/0034513 A1 * | 10/2001 | Rubinstein | A01N 1/02 604/410 |
| 2006/0175242 A1 * | 8/2006 | Dorian | A61M 1/0281 210/321.68 |
| 2007/0062885 A1 | 3/2007 | Strisino | |
| 2008/0311651 A1 * | 12/2008 | Coelho | A61M 1/0272 435/307.1 |
| 2011/0224062 A1 | 9/2011 | Pobitschka | |

FOREIGN PATENT DOCUMENTS

| | | | |
|---|---|---|---|
| DE | 27 41 398 A1 | 3/1978 | |
| DE | 10 2008 047068 A1 | 3/2010 | |
| GB | 1 591 989 A | 7/1981 | |
| WO | WO-84/02091 A1 | 6/1984 | |
| WO | WO 8402091 A1 * | 6/1984 | ............ A61M 1/029 |

OTHER PUBLICATIONS

International Preliminary Report on Patentability for Application No. PCT/DE2012/000628; dated Oct. 24, 2013.
International Search Report and Written Opinion for Application No. PCT/DE2012/000628; dated Mar. 8, 2013.

* cited by examiner

*Primary Examiner* — Emily A Cordas
(74) *Attorney, Agent, or Firm* — Alston & Bird LLP

(57) ABSTRACT

The invention relates to a method for separating blood, to a separation container and to a system, wherein different blood fractions—erythrocytes (64), buffy coat (65) and blood plasma (66)—are obtained, wherein blood is introduced into a separation container (1) and is then centrifuged into different superimposed, fluidically connected sections of the separation container, specifically a top section (4) for receiving the blood plasma (66), a middle section (3) for receiving the buffy coat, and a bottom section (2) for receiving the erythrocytes (64). The aim of the invention is to optimize the extraction of buffy coat. Said aim is achieved by means of the method and the separation container, wherein the optimization is geared to obtaining a defined phase boundary, and by means of the system, wherein the optimization is geared to achieving freedom from contamination from the time the blood enters the separation container and obtaining an easy-to-handle freezer container for cryopreservation. By means of the haematocrit of the blood supplied, the future packing volume of the erythrocytes (64) to be centrifuged is determined. Furthermore, the capacity of the bottom section (2) is adjusted to the expected packing volume of the erythrocytes after the centrifuging in such a manner that the phase boundary (5) forming during centrifuging between buffy coat (65) and erythrocytes (64) is positioned in a region of the middle section (3) of the separating container (1) adjacent to the bottom section (2), and finally the amount of blood supplied is introduced in the exact volume into the separation container (1), taking into account the expected packing volume of the erythrocytes (64). The separation container (1) enables the method to be carried out. The system is kept closed and avoids interaction with the environment.

20 Claims, 11 Drawing Sheets

METHOD FOR SEPARATING BLOOD, SEPARATION CONTAINER FOR A BLOOD CENTRIFUGE, SYSTEM FOR FILLING A FREEZER CONTAINER

The invention relates to a method for separating blood, wherein different blood fractions—erythrocytes, buffy coat, and blood plasma—are obtained, wherein blood is introduced into a separation container and is then centrifuged into different, fluidically connected sections of the separation container arranged above one another, specifically a top section for receiving the blood plasma, a center section for receiving the buffy coat, and a bottom section for receiving the erythrocytes.

Moreover the invention relates to a separation container for a blood centrifuge, in particular for performing the method, having a bottom section for receiving erythrocytes, having a center section for receiving buffy coat, and having a top section for receiving blood plasma, wherein the center section has a smaller cross-sectional dimension than the top and bottom sections, wherein the sections are fluidically connected and wherein the bottom section is separable from the center section.

Finally, the invention relates to a system for filling a freezer container with a blood fraction obtained after centrifugation, specifically buffy coat, and for preparing the buffy coat for the purposes of cryopreservation in the freezer container, in particular using and embodiment of a separation container in accordance with the invention and in particular executing an embodiment of the method in accordance with the invention.

Blood may be separated into different blood fractions by means of a centrifuge in that the centrifuge is rotated rapidly at certain speeds and for a certain period of time. After centrifugation, the nature of the blood in the separation container has changed. The individual components have divided into blood plasma, which primarily comprises protein and water, buffy coat, and erythrocytes. Buffy coat includes all leucocytes and the majority of thrombocytes. The erythrocytes are the heaviest, followed by the leucocytes and thrombocytes in the buffy coat and in the blood plasma.

Breaking blood down into its components is necessary not only in diagnostic processes and other laboratory applications, but also in the field of cryopreservation of umbilical cord blood. Freezing it is very costly. The space in cryogenic devices in blood banks is limited and expensive because the samples must be cryopreserved using liquid nitrogen. So there is a general need to reduce volume. The item being cryopreserved should be stored in bags having the smallest possible volume. Buffy coat is of interest as an item for cryopreservation stem cells may be obtained from it. The separated buffy coat fraction must be rendered storable so that it can be supplied to the patient later. Rendering it storable and cryopreservation is performed using the chemical compound dimethyl sulfoxide, hereinafter referred to as DMSO, in a deep-freeze container. The chemical compound DMSO is used to concentrate the cell fluid in the preparation in order to equalize differences between different osmotic pressures there. This protects the buffy coat or the cell substance from destruction/from the cells bursting. As an alternative to pure DMSO, it is also possible to use a pre-mixed cryopreservation agent, such as e.g. DEXTRAN 40.

After centrifugation, a phase boundary has formed between the buffy coat fraction of interest here and the erythrocytes. The position of the phase boundary is always different, depending on the properties and amount of blood. This makes the targeted removal of the buffy coat more difficult, which means that the yield is not optimal. The roll of the boundary between blood plasma and buffy coat is not as significant. As a rule, the blood plasma also spreads in the center section, since the amount of buffy coat is very small. Buffy coat is usually also mixed with blood plasma and other substances when the substance to be cryopreserved is prepared.

DE 10 2008 047 068 A1 describes a centrifuge that has a separation container with two receptacles that are fluidically connected to one another via a flexible plastic tube. There are a top section, a center section, and a bottom section into which the different fractions of the blood are centrifuged. It is important to maintain closed systems with respect to supply and discharge devices and separation container and sterile connections. The buffy coat is collected in the center section and in the plastic tube, and the center section may be separated by clamping the bottom section in which the erythrocytes collect. There, although the blood to be centrifuged may be added in an exact volume, no defined phase boundary is attained in this prior art. The collection of the buffy coat in the center section, into which blood plasma also spreads, occurs according to experience, and the volume of the center section is sometimes used more and sometimes used less.

A separation container, which is provided, however, exclusively for the sedimentation process, and also three sections—top section, center section, which has a smaller cross-section than the two other sections, bottom section—is known from DE 2741398 A1. It describes that top section and bottom section have a volume ratio that is essentially equal to the volume ratio between erythrocytes and plasma in the blood. The surface that separates the plasma from the erythrocytes should then be disposed in the center part or in the connecting line there. There is no description of where exactly the phase boundary runs. This document is also more concerned with estimates and there is no specification of the phase boundary with respect to different blood samples and quantities.

The underlying object of the invention is to provide a method and a separation container of the type being discussed and to provide a system, wherein obtaining buffy coat is optimized.

With the method and the separation container, optimizing is in particular directed at obtaining a defined phase boundary between the centrifuged erythrocytes and the centrifuged buffy coat in order to optimize the yield of buffy coat.

With the system, optimization is directed at freedom from contamination starting at the time when the blood has travelled into the separation container and at obtaining a manageable freezer container for cryopreservation, which are intended to optimize recovery of and moreover also transport and storage of the buffy coat. A freezer container that is filled with buffy coat under contamination-free conditions while avoiding contact with the environment and that is suitable for storage/cryopreservation in a blood bank is to be produced with the system. In particular the appropriate method steps, described here, are to be executed with the system, using a corresponding separation container, described here, for preparing at least one freezer container.

The aforesaid object relating to the method is attained using the features of patent claim 1. According to it, a method of the type being discussed is embodied such that the future packing volume of the erythrocytes to be centrifuged is determined using the hematocrit value of the supplied blood, in that the capacity of the bottom section is adapted to the expected packing volume of the erythrocytes after centrifugation such that the phase boundary forming between buffy coat and erythrocytes during centrifugation is positioned in a region of the center section of the separation container that is adjacent to the bottom section, and in that the quantity of supplied blood is introduced into the separation container in an exact volume, taking into account the expected packing volume of the erythrocytes.

The aforesaid object relating to the separation container is attained using the features of the embodiments disclosed herein. According to an embodiment described herein, a separation container of the type being discussed is embodied such that the capacity of the bottom section may be adapted to the expected packing volume of the erythrocytes after centrifugation such that the expected packing volume may be essentially completely accommodated by the bottom section and in that because of this the phase boundary between erythrocytes and buffy coat runs into a region of the center section that is adjacent to the bottom section.

The aforesaid object relating to the system is attained using the features of the embodiments disclosed herein. According to an embodiment described herein, the system has the following features:

A supply device for blood, a separation container, and a freezer container are provided;

The supply device for blood includes at least one anticoagulant supply and one sampling section and is connected in a sterile manner to the separation container;

The supply device for blood may be separated in a sterile manner from the separation container after the separation container has been filled and before the separation container is centrifuged;

The separation container has a bottom section, a center section, and a top section;

The center section may be transformed into a freezer container after centrifugation, with the top and bottom sections removed;

The center section or the freezer container may be connected in a sterile manner to a syringe, a supply device for DMSO, and a pressure equalization device;

The syringe, the supply device for DMSO, and the pressure equalization device may be separated in a sterile manner from the separation container after preparation of the buffy coat.

Proceeding from the prior art known from practice, with respect to the method it has been acknowledged that a different position of the phase boundary is obtained depending on blood properties and quantity, so that the targeted removal of the buffy coat is rendered more difficult. It is furthermore acknowledged that it is desirable for the phase boundary between erythrocytes and buffy coat attained by centrifugation to be embodied at a pre-determined position. The phase boundary should optimally run on the boundary between bottom section and center section of the separation container so that the center section is available exclusively for the buffy coat, where applicable for blood plasma, but not for the erythrocytes, and the yield is not reduced. Finally, it has been acknowledged that a pre-specified position of for the phase boundary may be attained when the future packing volume of the erythrocytes to be centrifuged is determined using the hematocrit value of the supplied blood, when the capacity of the bottom section is adapted to the expected packing volume of the erythrocytes after centrifugation such that the phase boundary forming between buffy coat and erythrocytes during centrifugation is positioned in a region of the center section of the separation container that is adjacent to the bottom section, and when the quantity of supplied blood is introduced into the separation container in an exact volume, taking into account the expected packing volume of the erythrocytes. The blood may be for instance umbilical cord blood or blood from the blood bank, to which anticoagulant has been added in either case.

For determining the hematocrit value, standard values may be evaluated and conclusions may be drawn from this regarding the packing volume of the cells in the blood sample. A much more precise determination of the hematocrit value may advantageously be determined by drawing a sample from the blood to be supplied. Using the hematocrit value obtained from a separate centrifugation in a simple separation container it is possible to determine the expected packing volume of the erythrocytes after centrifugation and then the inventive separation container may be supplied.

Based on measurements, the ratio between the hematocrit value and the packing volume of the erythrocytes after centrifugation is known. Together with the determined hematocrit value, it is possible to calculate what the packing volume of the erythrocytes will be after centrifugation. For instance, if there is a supply quantity of 100 mL of umbilical cord blood, it may be predicted that between 40 and 60 mL packing volume of erythrocytes should be expected. Thus a capacity between 40 and 60 mL must be provided in the bottom section of the separation container, which capacity the erythrocytes will occupy after the centrifugation.

The adaptation of the capacity of the bottom section to the expected packing volume of the erythrocytes may be realized using shape modifications. To this end, the bottom section may have compartments, for instance, that are clamped off or welded off or broken off. It is also possible for there to be an expansion of the bottom section, it being possible to connect pre-fabricated compartments using break-away valves. The adaptation of the capacity may also be attained using a filling measure. For instance, the bottom section may be filled with inert pellets until the remaining capacity is the right size. In any case, the buffy coat should be prevented from traveling into the bottom section or into the top section.

If regions of the bottom section are welded off, there is an irreversible change in volume. There may be some imprecision since the experimental factor—how long and how fast centrifugation will be—must also always be taken into account. If the packing volume is calculated just a bit too small, erythrocytes would travel into the center section. If this happens, erythrocytes may quickly be drawn off so that the erythrocyte level drops and the center section is free of erythrocytes again. If the packing volume adaptation is reversible, for instance when it is filled with pellets, they may be removed in the quantity needed or they may be displaced by clamping.

Horizontal scaling on the bottom section may be used to adapt the capacity of the bottom section to the expected packing volume for the erythrocytes after centrifugation. It would also be possible to use a bottom section that has different compartments with defined volumes and adapt in this manner.

Without adding an exact volume of blood to the separation container it is not possible to have optimal receiving of the erythrocytes in the bottom section. The blood may therefore be supplied preferably using vertical scaling on the separation container, the scaling extending across all three sections (top section, center section, bottom section).

To promote sedimentation, an additional substance, in particular hydroxyethyl starch solution, hereinafter referred to as HES, may be added to the blood prior to centrifugation. This addition may take place after the blood has been supplied to the separation container. The required quantity of HES may be calculated based on the quantity of blood supplied and may also be added in an exact volume. The addition of HES may be controlled using the vertical scaling.

Finally, the bottom section may be completely separated from the center section after centrifugation. Preferably sterile welding off or clamping off is used for the separation method. When the bottom section is separated, it is most important that the separation occurs without any loss of buffy coat, i.e. it is preferable to have very small quantities of erythrocytes in the buffy coat during the separation process rather than to have loss of buffy coat. Naturally the center section is also separated from the top section. In this way it is possible to use the buffy coat, which here is more valuable, to perform additional method steps for obtaining stem cells.

The transport and storage of the buffy coat collected in the center section are very important for continuing the present invention. In accordance with one preferred exemplary embodiment, the collected buffy coat may be released into a freezer container, the component of which is the center section itself. To this end the connection to the region of the freezer container that was separated earlier, during centrifugation, is established. In this preferred exemplary embodiment, the structural height is saved, since the inventive separation container must fit into a standardized centrifuge beaker.

In accordance with one alternative exemplary embodiment, however, the buffy coat may also travel out of the center section into a freezer container that is preferably arranged on the top section of the separation container and is fluidically connectable thereto, for instance via a sterile connected line. After centrifugation and after the bottom section has been separated from the center section, the fluidic connection may be established between freezer container and center section. In this exemplary embodiment it is advantageous to perform centrifugation two times, the second centrifugation taking place in the opposite direction after the bottom section has been separated and moving the buffy coat into the top section and finally into the fluidically-connected freezer container attached thereto and moving the lighter blood plasma into the center section. The bottom section, which is still present but is separated for instance by a weld seam, may go through the second centrifugation process, as well. The separated bottom section may be folded over, since during the second centrifugation the freezer container is filled directly and the structural height of the standardized centrifuge beaker must be taken into account. The connecting line between freezer container and separation container may be held in a stabilizer.

With regard to centrifugation acceleration it should be noted that a lower speed is adequate for blood to which HES has been added and for which a second centrifugation is planned. During the second centrifugation the acceleration must be increased significantly in order to adequately concentrate the buffy coat in the section provided for it.

In accordance with the inventive refinement of the method, the processes relating to the centrifuged buffy coat in the freezer container may be configured such that, as for the bottom section previously, the capacity of the freezer container is adapted to the visible quantity of buffy coat after centrifugation. The adaptation may be made for example by separating compartments of the freezer container. Separation of the fluidically connected compartments may be facilitated using bars incorporated inside the freezer container. It is clear that after the capacity has been adapted and after it has been filled with the buffy coat and where applicable at least one other substance, the freezer container must be completely sealed off and finally separated from the top section, as well. In this manner small, easily managed freezer containers are created that may be optimally filled and do not take up any excess space in the expensive blood banks/cryopreservation devices. When the capacity of the freezer container is adapted for receiving the buffy coat, it should be taken into account that additional substances, in particular DMSO, where applicable blood plasma, or a mixture thereof, must be taken into account when the capacity is being adapted.

Alternatively to adding a substance via a supply line, a reservoir with DMSO may already be provided in advance in the freezer container. For instance, a region on the freezer container may be clamped off to produce the reservoir. If the freezer container has compartments, the reservoir may also be formed by at least one compartment. After the freezer container has been filled with buffy coat, the connection between the compartments, some filled with DMSO, some filled with buffy coat, may be established and everything may be mixed in the freezer container.

If the quantity of buffy coat is not adequate for a standard volume of the freezer container, blood plasma may be added as filler. The blood plasma may also be added to a reservoir of the freezer container. Alternatively, a mixture of DMSO and blood plasma may be added to the reservoir.

Contamination is undesired during the centrifugation of blood samples and all subsequent steps. The risk of contamination may be very sharply reduced if the separation container of the centrifuge, which separation container is sealed to the outside, as is known, is filled and removed excluding the atmosphere. Contact with the atmosphere may be precluded if the separation container is filled with blood via its supply connector, which may be connected in a sterile manner. Other substances should also be introduced to the supply device for blood, to the separation container, and to the freezer container via sterile connections. The separation container, the freezer container, and all other removal and/or supply devices having reservoir and/or mixing and/or metering and/or transport functions should be connected to one another in a sterile manner.

The supply device for blood may include a blood collection container into which the blood removed is fed via cannulas. The blood collection container may also have a sterile connector and be sealed against the environment. In this manner, it is possible, even inside the supply device, which cannot form a closed system due to the cannulas that are open for removing blood, to produce a component that is sealable and may also be a component of a closed system after the blood has entered the blood collection container. The blood collection container may be in the form of a collapsed bag and therefore may be filled with blood without displacing air.

In contrast to a collapsed bag, which is two-dimensional when unfilled and does not become three-dimensional until it has been filled, the sections of the separation container provided for the blood and its fractions may be three-dimensional from the beginning and thus advantageously provide a much larger capacity for the blood. The disadvantage of the collapsed bag lies in the limitation of the volumes of blood and where applicable adjuvant substances, connected to the need for a plurality of centrifuging steps, separation of the blood quantity originating from one source, and its labeling and administration. If a collapsed bag is also divided into chambers, the capacity is even further reduced. The collapsed bags have standardized dimensions so that there is little clearance. For the invention it is essential that the blood travels into three-dimensional separation container sections, since this is how variable fill volumes may be attained. Due to the advantageous three dimensionality of the separation container sections, it is where applicable to variably centrifuge larger quantities of blood, and possibly adjuvant substances, from the beginning in one work process. Fill volumes up to approx. 500 mL may be realized.

All components that are brought into contact with one another in a sterile manner or whose connection may be interrupted or that may be completely separated from one another in a sterile manner may advantageously form a closed system. A closed overall system that may ultimately be broken down into individual closed systems again is formed from the individual closed systems after they have been connected in a sterile manner. It is obvious that the risk of contamination is advantageously reduced to the step for removing blood.

In practice, it is specifically the addition of DMSO that always occurs with the container that holds the buffy coat being opened. This can result in contamination. This risk is countered by working in expensive cleanrooms. The inventive exemplary embodiment, which is also reflected by the inventive system, advantageously makes it possible to reduce costs since it is also possible to work in the laboratory if all of the components that are downstream of the supply device or the blood supply line to a blood collection container of the supply device are components of a closed system. The blood collection container may be a collapsed bag that does not become three dimensional until the blood has been fed in. The lines are welded in a sterile manner to connectors that may be opened and closed so that the closed system may be created by closing the blood supply line.

In the preferred exemplary embodiment in which the blood is fed into the separation container that is three dimensional from the beginning, the closed system starts with the closure of the separation container after filling. The air present in the separation container may be displaced into an additional container, or may be conducted into a blood collection container if one is provided. In the latter case, there is system internal circulation of air/inert gas from the separation container to the blood collection container and from the blood collection container to the separation container.

With respect to the addition of DMSO, syringe and DMSO vial are included inside three-dimensional containers or are covered such that the user may still, through the separation wall, use the syringe and open and place the vial. The lines are also connected in a sterile manner to the container/covering so that there is no contact with the outside world. The other substance to be added, HES, is also contained in a container that takes up a space in which the substance is contained and that has lines attached in a sterile manner. Thus system is not opened. On the contrary, the substances are transported without interacting with the environment, and the air or inert gas also remains in the system, which includes precautions for equalizing pressure. Air and gas are specifically not discharged via filters, because there is always the risk of gas and viruses entering the system. The displaced air is only removed from the system if components are separated in a sterile manner according to the successive method steps.

Outside of the closed system, as well, in the region of the supply device, anti-coagulant is stored in a container that takes up a space for receiving the anticoagulant and has lines connected in a sterile manner.

As soon as the separation container is filled with blood, the supply device for blood is disconnected in a sterile manner. In contrast, the removal and/or supply devices with reservoir and/or mixing and/or transport and/or metering functions for DMSO, and the entire syringe assembly, blood plasma, HES, where applicable inert pellets, and the separation container including all connecting lines are added to a standardized centrifuge beaker. The connecting lines are connected to the components in a sterile manner, but secured using tube clamps so that the fluidic connection cannot be created until the tube clamps have been removed. If the separation container is a component of a closed system, a pressure equalization device on the separation container or on the covering of a syringe that supplies DMSO could also be added to the centrifuge beaker. This also applies for a receptacle for erythrocytes, which receptacle may be arranged at the bottom section of the separation container and receives excess erythrocytes after the centrifugation if the phase boundary or the buffy coat level is too high in the center part and a deviation from the calculation occurs due to the centrifugation process.

No later than after the freezer container has been filled with buffy coat and where applicable DMSO, where applicable blood plasma, other components of the separation container are removed/welded off from the freezer container in a sterile manner. The freezer container may now be supplied for the cryopreservation procedure in the blood bank. If the freezer container has compartments, parts of the freezer container may be supplied for different uses and warehousing sites. In accordance with another exemplary embodiment, the freezer container may also be separated from the separation container or from the rest of the separation container prior to filling with DMSO.

With respect to the inventive separation container, it has become known that due to the adaptability of the capacity of the bottom section to the expected packing volume of the erythrocytes after centrifugation, the phase boundary may be positioned precisely, specifically in a region near the boundary between bottom section and center section, and thus the buffy coat yield in the center section may be optimized.

A vertical scaling that extends across all of the sections may be provided on the separation container so that an exact volume of the blood sample may be added. A horizontal scaling may be provided on the bottom section for pre-adapting the capacity of the bottom section corresponding to the expected packing volume of the erythrocytes after centrifugation.

Clamping devices may be attached to the bottom section in order now to align, especially to reduce, the capacity of the bottom section to the expected packing volume. In accordance with another embodiment, the bottom section may have fluidically connectable compartments that may be welded off to reduce the volume. In this exemplary embodiment, wherein the bottom section is constructed of compartments, the compartments may be fluidically connectable as needed via break-away valves. This embodiment also makes it possible to increase the volume. It may also be possible simply to weld off regions of the bottom section.

In particular if the reduction in volume is irreversible, but also in general, a receptacle for drawing off centrifuged erythrocytes may be provided on the bottom section for keeping the center section free of erythrocytes. The receptacle for erythrocytes may be connected in particular in a sterile manner to the bottom section-side connector of the separation container. If the phase boundary is placed too far up in the center part after centrifugation, erythrocytes may be quickly drained from the bottom section into the receptacle. In accordance with this possibly necessary receiving of erythrocytes, it may be possible to separate the receptacle, preferably in a sterile manner, from the separation container.

Finally, a supply device may be provided for filler, especially inert pellets, which device is fluidically connectable to the bottom section, so that to reduce the volume thereof filler may be introduced into the bottom section.

So that the acknowledged very advantageous three dimensionality of the sections of the separation container provided for the blood fractions may be retained, the separation container may be produced from a manufacturing technology point of view from two films that are disposed above one another and that have deep-drawn regions for forming the different sections and a blank region disposed therebetween. The blank region outside of the sections for the blood fractions may be flat and welded. In this manner the various sections for receiving the different blood fractions—bottom section, center section, top section—are created in the deep drawn regions, and blank regions are also created that take up almost no space but make it possible for supply devices for DMSO, HES, and filler to be accommodated in the centrifuge beaker in addition to connecting lines. Provisions may be made on the edge of the blank region so that the separation container may be attached in a tray which then is inserted into the centrifuge beaker. Being three-dimensional from the beginning, the inventive separation container is suitable, with or without blank regions, for a normal blood bank centrifuge and fits in standardized centrifuge beakers, even if additional components of the system must also be accommodated in the centrifuge beaker.

Various slit-like openings may be provided in the blank region, through which openings clamping devices, such as for instance clamping tongs, may be inserted. This is necessary in the region of the center section so that it is possible to clamp at least below the phase boundary and the buffy coat may be secured, but also in the region of the bottom section and, in a preferred embodiment of the inventive separation container also in connection with transforming the center section to the freezer container. It may also be possible to insert a welding device through the slit-like openings for separating the sections from one another or for separating regions of a section, in particular the bottom section when the volume is reduced.

Suspension units may be provided in the centrifuge beaker in which fastening means of the separation container are anchored. This is primarily the edge of the blank region that is adjacent to the top section and closes upward and may have a series of through-openings. The latter may also be useful for suspension units on stands while other method steps are being executed. In addition, a stabilization part or an insert that supports the inventive separation container and that has the proper shape may be inserted into the centrifuge beaker.

With respect to the goal of supplying buffy coat for cryopreservation, one advantageous refinement of the separation container provides that the separation container includes a freezer container. For safety reasons, that is, as a redundancy measure, two freezer containers that are both filled may also be assigned to one separation container. This is advantageous in terms of storing the buffy coat at two different locations. However, it is also possible to have a freezer container with compartments that may be separated at a later time.

According to a first, preferred alternative, the freezer container may be an integral component of the center section of the separation container. This is a space-saving variant that also has plenty of room in a standardized centrifuge beaker. By welding off the top and bottom sections after centrifugation and after the buffy coat and where applicable other substances have been admitted into the freezer container, one freezer container is then available in which, seen from a different viewpoint, the center section of the former separation container is integrated. The freezer container may be separated from the blank field described above via a perforation line.

Alternatively, the freezer container may also be assigned to the separation container and may be fluidically connectable thereto via lines that may be opened and closed. The connection may be made on the top section, a second centrifuging process then being necessary in the opposing direction, as described in the foregoing with reference to the method.

In particular if the object of working in a closed system is being pursued, in accordance with one preferred embodiment, without interaction with the environment, that is, with no filters, a pressure equalization device for air or inert gas that is connected in a sterile manner, and may also be separated in a sterile manner, is assigned to the separation container. Referring to the exemplary embodiment, wherein the center section is transformed into a freezer container, the pressure equalization device may be connected in a sterile manner for instance to the center section of the separation container. In one exemplary embodiment with a blood collection container, the latter may also be used for pressure equalization or for displacing air/inert gas. A pressure equalization device is also necessary when the separation container from the beginning has three-dimensional regions for forming top, center, and bottom sections. Trapped air always plays a part in three-dimensional containers. Trapped air may have a negative effect on the substance being frozen and on the freezer container. If air travels into the freezer container, there may be stresses and the freezer container may crack, especially at the low freezing temperatures of nearly −200° C.

It may be possible to adjust the capacity of the freezer container to the expected yield of centrifuged buffy coat from the center section, where applicable to the addition of at least one additional substance. To this end, the freezer container may have fluidically connectable compartments, in particular with bars incorporated between the compartments, which compartments are separable, in particular may be welded off in a sterile manner, for reducing the volume.

As already described in the foregoing in connection with the method, the blood may be removed from an umbilical cord or it may be anticoagulated blood from a blood bank. The blood may be supplied at the bottom section of the separation container via a connector that may be connected in a sterile manner. In the case of umbilical cord blood, the supply device may have at least one cannula for taking blood, a connecting line arranged thereon, and at least on branching for connecting a supply device for anticoagulant to the connecting line. In addition, a sampling section may be provided on the connector on the separation container as a dead-end branch of the connecting line. The blood sample taken from the sampling section may be used for determining the hematocrit value in order to make a patient-specific determination about the expected packing volume of the erythrocytes after centrifugation. The sampling section may have different dimensions, in particular length dimensions. In this manner samples may be made available in addition to the hematocrit value determination.

To be able to keep the risk of contamination very low, the cannula may have a perforatable sterilized latex covering that is not punctured until the umbilical cord is punctured with the cannula. The window of time for environmental contact is thus kept very small and the risk of contamination is reduced.

A supply device for HES for promoting sedimentation may be connected via a branching on the connecting line of the supply device for blood. Alternatively, the supply device may also include a blood collection container and the supply device for HES may preferably be connected in a sterile manner to the blood collection container. In accordance with another embodiment, the HES may also be supplied directly to the separation container via a connector. The substance may be contained in a reservoir with connector or even in a vial that is not opened until it is needed. In the latter case, a container that encloses the vial would be provided as desired in the closed system, analogous to the DMSO supply device. In this case, as well, care must be taken that displaced air remains in the closed system, for instance via a pressure equalization device connected in a sterile manner. It would then be possible to do entirely without HES if the centrifugation is performed at higher G's (acceleration rates), i.e. at higher rotational speeds.

Whether separate or arranged on the center section of the separation container, the freezer container, and where applicable the top section of the separation container, may be connected to additional removal and/or supply devices with transport, reservoir, and/or mixing and/or metering functions. For reasons already discussed, the freezer container may be connected to a supply device for DMSO. There the DMSO may be available via a break-open vial. After breaking, the DMSO may be removed manually via a particle filter/round filter using the syringe and then pumped to the freezer container using a syringe pump. The DMSO is not added until after the centrifugation. The top section of the separation container may be connected to a removal device for removing blood plasma. To attain a standardized volume in the freezer container during cryopreservation, blood plasma may also be removed from the top section, for instance using the syringe, and added to the freezer container.

The separation container, the supply device for DMSO and the syringe, the supply device for HES (regardless of whether attached to the separation container, a blood collection container, or the supply line to the separation container), and where applicable the blood collection container of the supply device for blood may be components of a closed system. The individual components may be included inside of containers that are embodied as sterile coverings and do not permit any interaction with the environment. The individual components may be connected in a sterile manner to form the closed system. For all supply and removal devices, a system permits a common transport and mixing solution. This relates in particular to the syringe, which is provided for transporting DMSO, where applicable blood plasma, where applicable HES, and also acts as a mixing container, in particular for blood plasma and DMSO.

For reducing the system, depending on the method progress it may be possible to separate the individual components from one another in a sterile manner. Tube clamps may be provided for reversibly interrupting the fluidic connection. In the aforesaid embodiment, the idea of the closed system, apart from the blood removal as the single "open" point, is extremely important for the invention, since contamination is nearly impossible. Contamination can only occur during blood removal. No further contamination can occur once the blood is introduced into the separation container in accordance with one embodiment or into the blood collection container in accordance with another embodiment.

One refinement of the inventive separation container, which refinement is essential to the invention, is that at least one identification number is applied to the bottom section, center section, and top section of the separation container, and where applicable necessary to a sampling section. The sampling section may be a dead-end branch from a connecting line that leads to the separation container. In accordance with one embodiment, the sampling section may also branch off on a connecting line that is connected to the blood collection container and leads to the separation container.

These identification numbers advantageously avoid complex subsequent identification. From the beginning there is a relationship between blood removal, and thus patient, and the correct patient-related hematocrit value measurement and finally the freezer container that has the same identification numbers, thus eliminating the risk of incorrect associations.

The description of the method and its embodiments also relates to the separation container, so that reference is also made to the statements made about the separation container for explaining it.

With respect to the inventive system, it has been acknowledged that the inventive separation container, which includes a freezer container, and the inventive method, which includes filling the freezer container with buffy coat, may be used within a system that permits freedom from contamination after the blood removal step. Thus, contamination can only occur at the beginning of the method, and cannot occur thereafter. In addition, using the system a means may be provided, the components of which are gradually reduced after successive execution of the various method steps until the freezer container with the prepared buffy coat is all that is left. The system is directly technologically related to the inventive method and the inventive separation container in accordance with certain embodiments. Moreover, however, it may also in principle be used without the step of prior hematocrit value measurement and volume manipulation on the bottom section of the separation container, especially if a receptacle is provided for erythrocytes.

Particularly preferred is a system in which the supplying of the blood includes a blood collection container. In this case, the anticoagulant may be added initially such that it mixes with the removed blood that is supplied later. In addition, in a subsequent step the blood supply line to the blood collection container may be rinsed with anticoagulant and thus the last drops of blood may be transported to the blood collection container. The removed blood is thus collected in an essentially loss-free manner. If the blood collection has concluded, the supply line may be welded off in a sterile manner and the system, less the cannulas and the anticoagulant container, may be transported to the blood bank. There the system is suspended on a stand. There the blood collection container also proves advantageous since now it is very simple to add blood initially to a sampling section and later to the separation container. With respect to the embodiment of a closed system, after the blood collection container has been closed and, where applicable, the HES has been added, refer to the description of the method and separation container.

There are now various options for advantageously embodying and refining the teaching of the present invention. There are claims following patent claim 1, and there is the following explanation of five exemplary embodiments of the inventive separation container and two exemplary embodiments of the inventive system with drawings. Generally preferred embodiments and refinements of the teaching shall be explained in the context of the explanation for the provided exemplary embodiments of the invention. In the drawings:

FIG. 1 is a diagram of the inventive separation container in accordance with a first exemplary embodiment, the freezer container being allocated to the center section;

FIG. 2 is a diagram of an elevation of a first example of an inventive system having a supply device for blood, a separation container in accordance with a second exemplary embodiment, the freezer container being attached to the separation container, and having other options for adding blood plasma and HES and for adding blood plasma and DMSO prior to the blood being removed from the umbilical cord;

Figure 10:
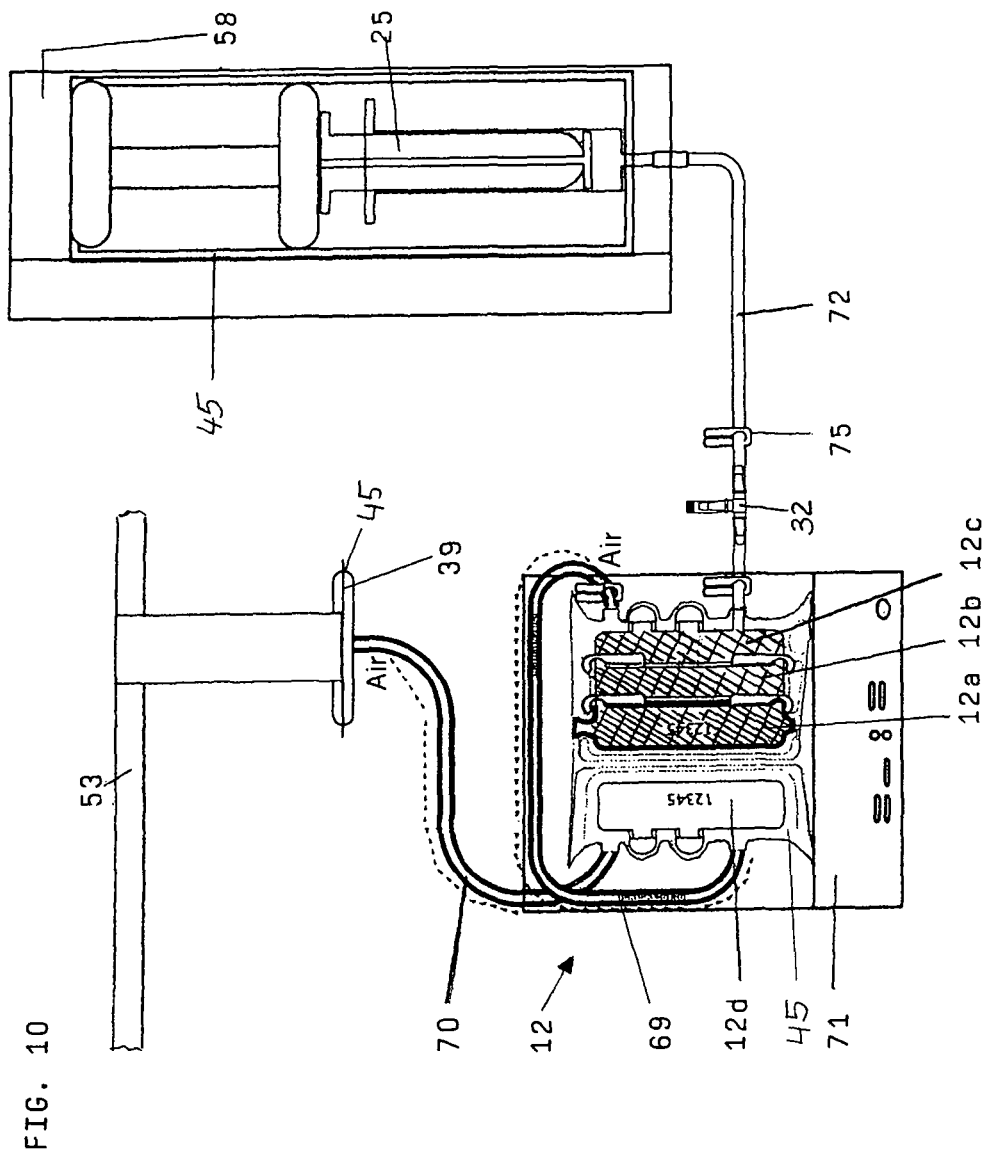
FIG. 10 is a diagram of a top view of a system from FIG. 9, but with a DMSO supply device that has been welded off, relating to DMSO addition via the syringe.
Figure 12:
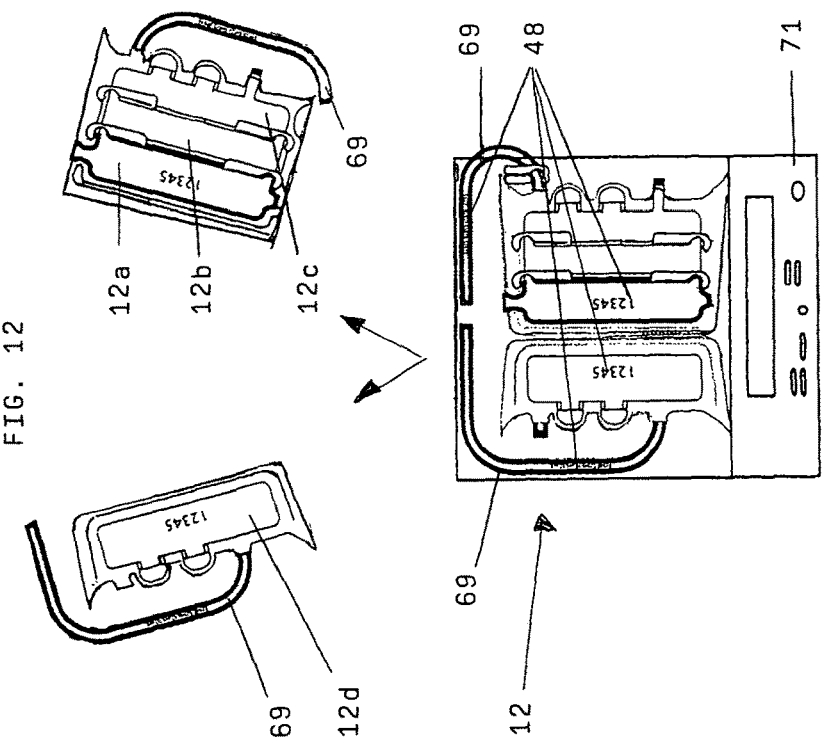
Figure 11:
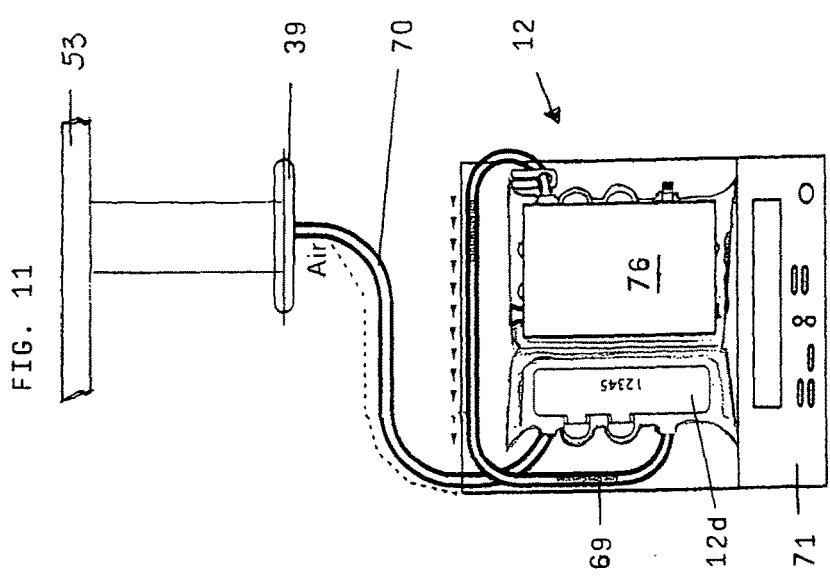

FIG. 11 is a diagram of a top view of the system from FIG. 10, but with a DMSO line that has been welded off in a sterile manner, relating to the distribution of the mixture of buffy coat, blood plasma, and DMSO in all compartments of the freezer container by means of a die; and, FIG. 12 is a diagram of a top view of the system from FIG. 10, but with an air line that has been welded off in sterile manner and a connecting line that has been separated in a sterile option and with the option of dividing the freezer container into two parts.

FIGS. 1 through 8 depict a separation container 1 for a blood centrifuge having a bottom section 2 for receiving erythrocytes 64, having a center section 3 for receiving buffy coat 65, and having a top section 4 for receiving blood plasma 66, the center section 3 having a smaller cross-sectional dimension than the top and bottom sections 2, 4, the sections 2, 3, 4 being fluidically connectable to one another and the bottom section 2 being separable from the center section 3.

In accordance with the invention, the capacity of the bottom section 2 may be adapted to the expected packing volume of the erythrocytes 64 after centrifugation such that the expected packing volume may be essentially completely accommodated by the bottom section 2 and because of this the phase boundary 5 between erythrocytes 64 and buffy coat 65 runs in a region of the center section 3 that is adjacent to the bottom section 2.

Figure 2:
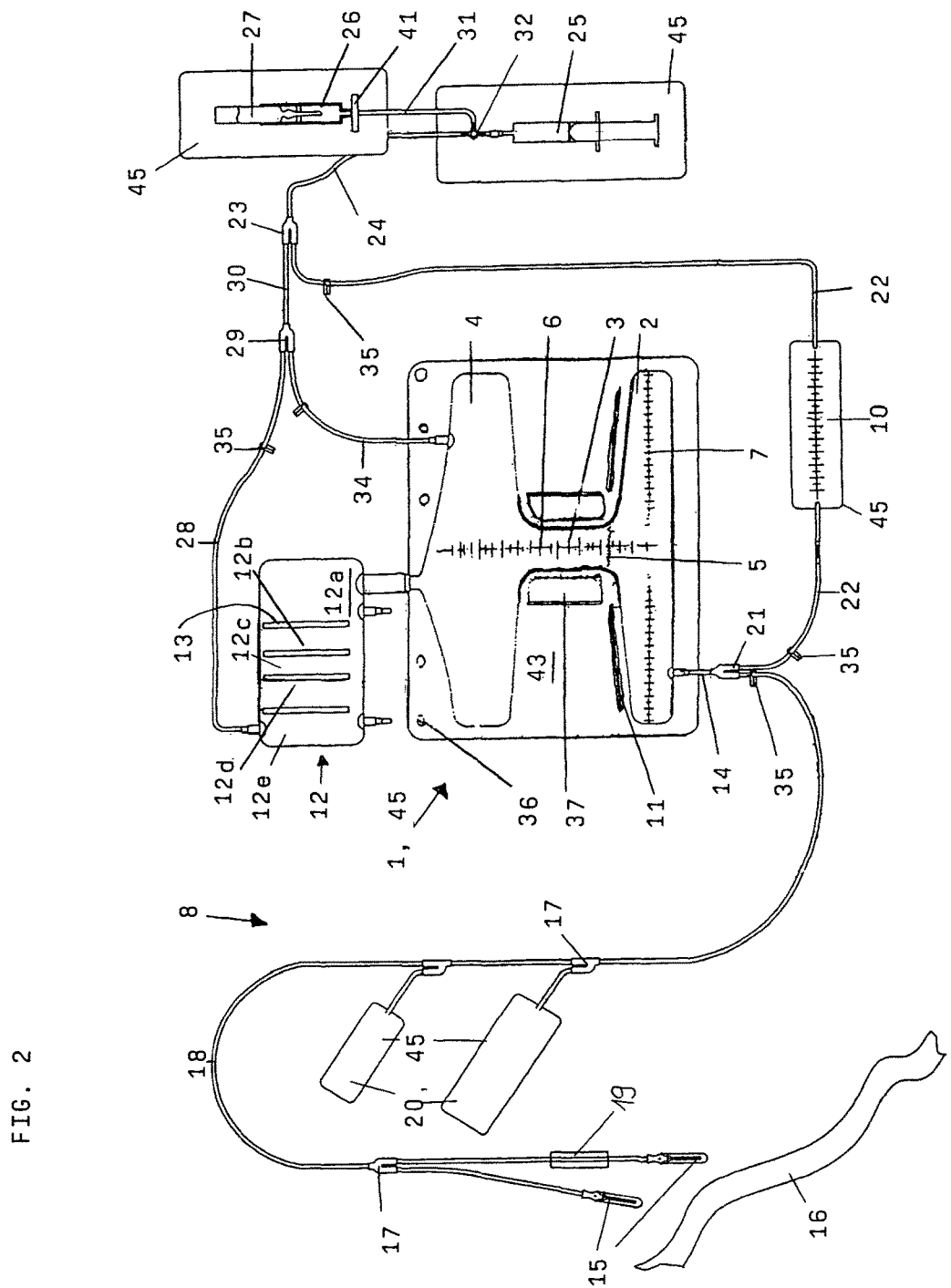
Figure 3:
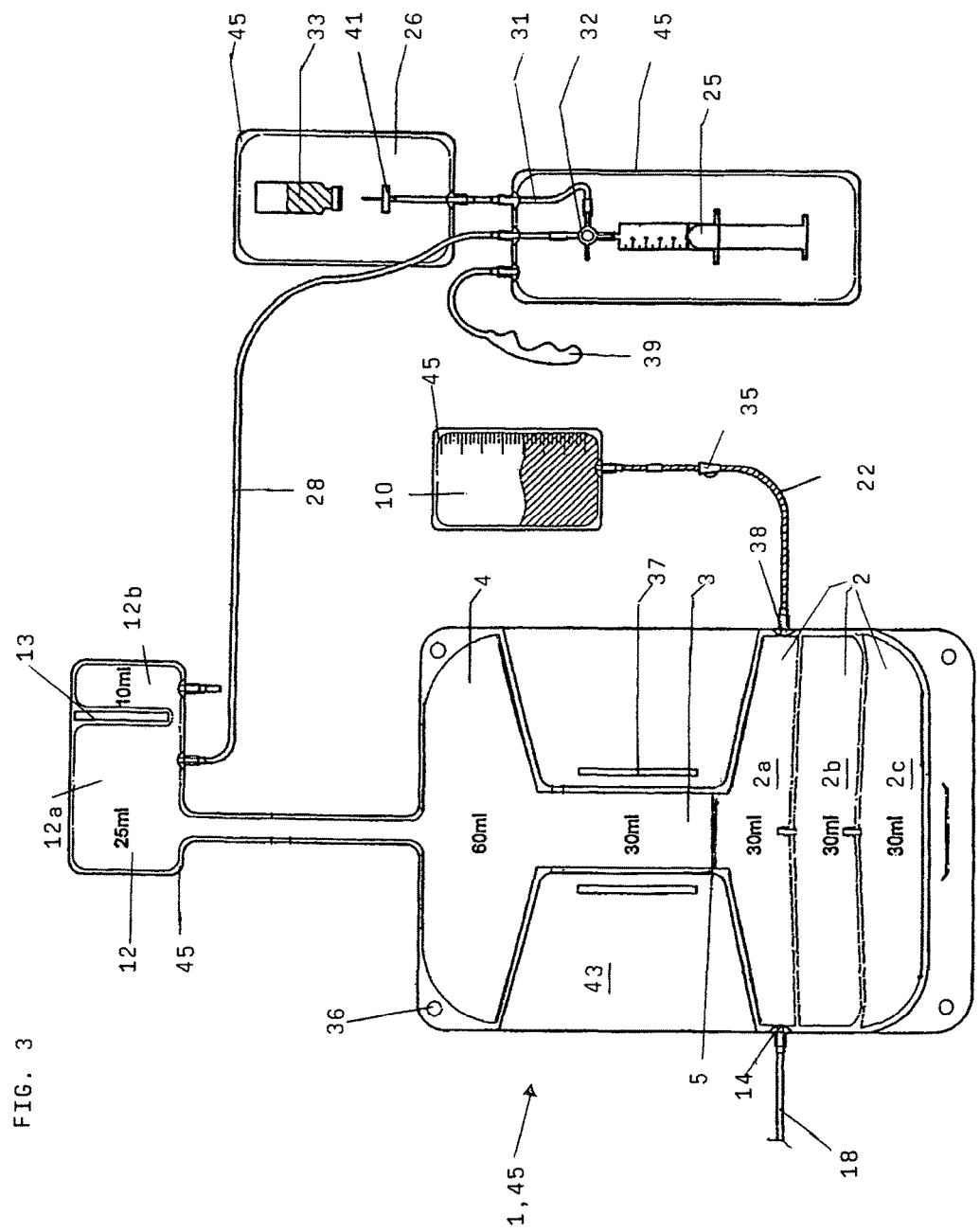
FIG. 3 is a diagram of an inventive separation container in accordance with a third exemplary embodiment, the freezer container being attached to the separation container and there being options for adding DMSO and HES.
Figure 4:
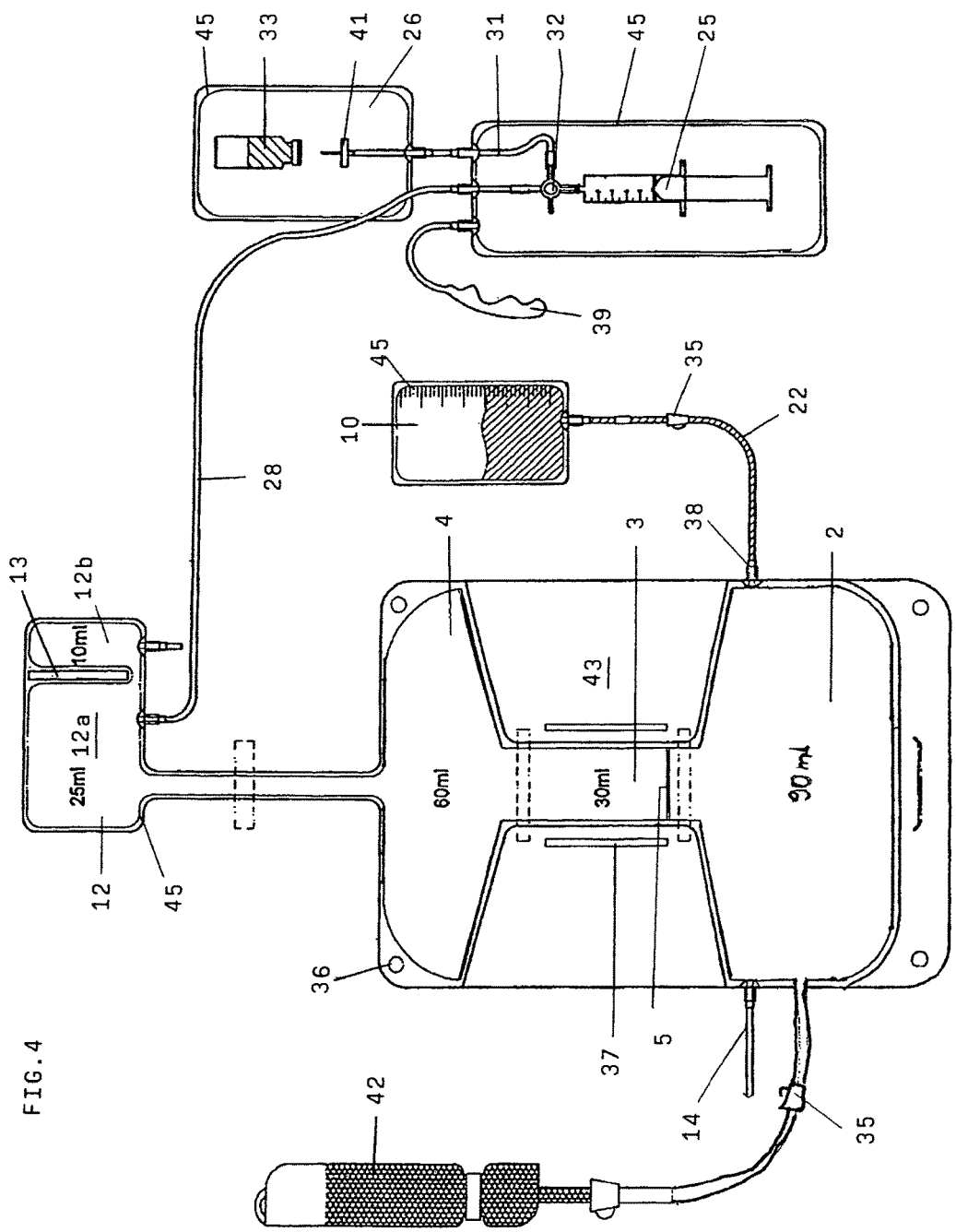
FIG. 4 is a diagram of an inventive separation container in accordance with a fourth exemplary embodiment, the freezer container being attached to the separation container and a filler supply for reducing the capacity of the bottom section being provided.

In accordance with the first and second exemplary embodiments of the separation container 1, a vertical scaling 6 for determining the fill volume of the blood to be supplied extends across all sections 2, 3, 4 on the separation container 1. FIG. 2 depicts a first example of an inventive system that includes a supply device 8 for blood via which the blood travels to the separation container 1. Not only can the blood quantity be monitored via the scaling 6, but also the substance HES, which in FIG. 2 is added from the supply device 10 or reservoir 10 in an exact volume. In FIGS. 3 and 4, HES is supplied from the reservoir 10 using gravity. A horizontal scaling 7 for preadjusting the capacity of the bottom section 2 corresponding to the expected packing volume of the erythrocytes 64 after centrifugation is provided on the bottom section 2.

In the third and fourth exemplary embodiments of the inventive separation container 1 depicted in FIGS. 3 and 4, volume information is printed on the separation container 1. In this case, the volumes are predetermined by the sections 2, 3, 4. A special feature depicted in the third exemplary embodiment is that the bottom section 2 is divided into three compartments 2a, 2b, 2c that may be used to increase the volume if the break-away valves (not shown in greater detail) disposed therein are opened. For the purposes of simplification, the scaling on the bottom and center sections 2, 3 in the fifth exemplary embodiment of the separation container 1 are not shown.

Figure 1:
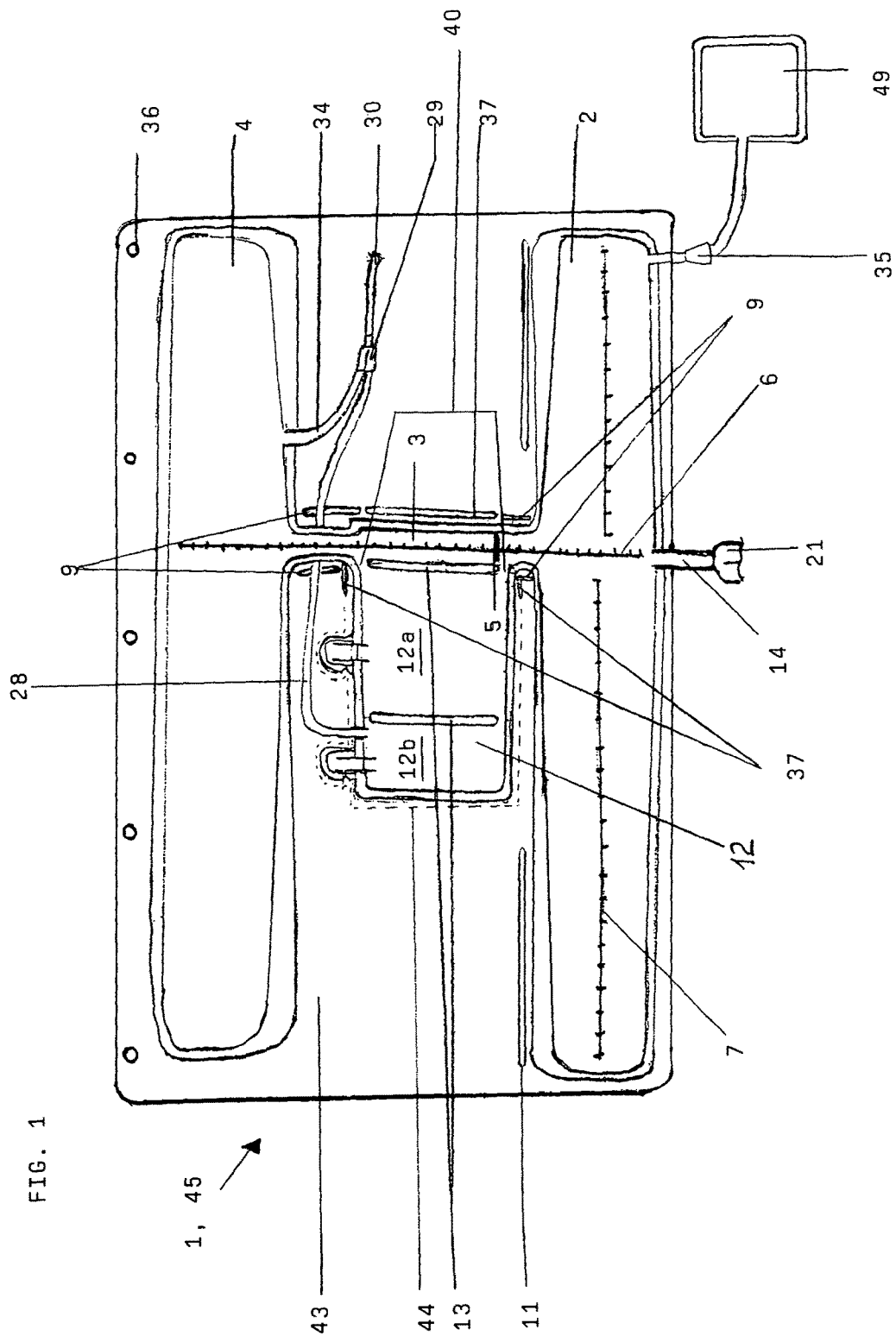

For adapting the capacity of the bottom section 2 to the expected packing volume of the erythrocytes 64, clamping devices may be attached to the bottom section 2 on the separation container 1 in accordance with FIGS. 1 and 2 via the recesses 11 to reduce the volume. In accordance with FIG. 6, in the fifth exemplary embodiment the unnecessary regions are separated using weld seams 56. In the first and fifth exemplary embodiments, as a provisional measure a receptacle 49 for excess erythrocytes 64 is provided in case the phase boundary 5 is unexpectedly high in the center section 3 and not, as desired, in the immediate vicinity of the bottom section 2. Collection of even the smallest quantities of erythrocytes 64 can be useful for correctly embodying and filling the freezer container 12.

The bottom section 2 of the separation container 1 in accordance with FIG. 3 has fluidically connectable compartments 2a, 2b, 2c for increasing the capacity. The compartments 2b, 2c may be welded closed to reduce the capacity.

In accordance with FIG. 4, the capacity of the bottom section 2 is reduced in that a supply device 42 for filler is provided that is fluidically connectable to the bottom section 2 so that for reducing the capacity of the bottom section 2 filler may be added thereto. The filler in this case is in the form of inert pellets.

The separation container 1 is manufactured from two overlaying films having three-dimensional regions, which in this case are obtained by deep-drawing, for embodying the different sections 2, 3, 4, where applicable of the freezer container 12 and a blank region 43 disposed therebetween, the blank region 43 preferably being flat and welded closed. Top section 4 and bottom section 2 have inner surfaces inclined toward the center section 3. Provided at the edge of the blank region 43 of the separation container 1 are fastening means 36 for holding the separation container 1 in a stable tray that may be placed into a centrifuge beaker 59. In this case the fastening means 36 are through-holes in which lab clamps of a stand 53 may also engage, as depicted for instance in FIG. 6.

All of the separation containers 1 include a freezer container 12. In the first and fifth exemplary embodiments, the freezer container 12 is an integral component of the center section 3. When the center section 3 is filled with the desired buffy coat 65, in the first exemplary embodiment the regions 40 that were closed until then are opened so that the center section 3 and the freezer container 12 initially with respect to compartment 12a are combined and the buffy coat 65 initially spreads in compartment 12a of the freezer container 12. The regions 40 are not opened until after centrifugation, and are only opened when the bottom and top sections 2, 4 have been effectively separated from the center section 3. To support separation of top and bottom sections, 2, 4, in the first exemplary embodiment cut-outs 9 are provided in the blank field 43, through which cut-outs 9 a clamping device may be inserted. When the freezer container 12 is filled as desired with buffy coat 65 and where applicable additional substances after the regions 40 have been opened, the freezer container 12 is closed and part of it is removed, part of it is cut from or welded from the blank region 43 along a perforation line 44.

FIGS. 2 through 4 depict a freezer container 12 that is allocated to the separation container 1 and is fluidically connectable thereto. In the second through fourth exemplary embodiments, the freezer container 12 is arranged on the top section 4 of the separation container 1; in these cases two centrifugations are performed in opposing directions.

In the first four exemplary embodiments, the freezer container 12 has fluidically connectable compartments 12a, 12b, and in FIG. 2 also 12c, 12d, 12e, between which a bar 13 or a plurality of bars 13 are incorporated. Depending on the quantity of obtained buffy coat in the center section 3, in FIG. 2 for instance the compartment 12e of the freezer container 12 may be separated to reduce the capacity. When the capacity is reduced, the addition of other substances must be taken into account. In the fifth exemplary embodiment, especially in accordance with FIG. 9, the freezer container 12 has compartments 12a, 12b, 12c, and 12d, compartment 12a corresponding to the center section 3 of the separation container 1.

A connector 14 for adding blood that can be connected in a sterile manner is provided on the bottom section 2. In the first four exemplary embodiments HES is conducted via the HES line 22 and via connector 14 or 38 into the bottom section 2. In the fifth exemplary embodiment HES is added to an upstream blood collection container 46.

FIG. 2 depicts the separation container 1 incorporated into the inventive system at the time the blood is taken from the patient, which system includes supplying the blood, subsequent centrifugation, subsequent preparation of the buffy coat in the freezer container 12, and the step-wise elimination of all system components except for the freezer container 12. The supply device 8 for supplying the blood includes two cannulas 15 for removing blood from the umbilical cord 16, each having a perforatable, sterilized latex cover (not shown in greater detail). Proceeding from a Y-shaped part 17, the cannulas 15 form the ends of a connecting line 18. A cannula protection unit 19 protects the second cannula 15. Provided on the connecting line 18 are two additional Y-shaped parts 17 via which the supply devices 20 for anticoagulant to prevent blood clots are connected to the connecting line 18. The end of the connecting line 18 opposite the cannulas 15 opens into another Y-shaped part 21 via which the separation container 1 is supplied via the connector 14.

The HES line 22 of the reservoir 10 or of the supply device 10 for HES leads via the second connector of the Y-shaped part 21 to the connector 14. The other end of the HES line 22 opens into another Y-shaped part 23 that leads via a connecting line 24 to a syringe 25 that is used for substance transport and where applicable also mixing processes and metering and which is also responsible for the movement and pumping of DMSO and blood plasma 66.

In FIGS. 3 and 4 HES is fed into the bottom section 2 directly via its own connector 38.

In the first two exemplary embodiments of the separation container 1, the freezer container 12 is connected indirectly via the connecting line 28 to a supply device 26 for DMSO, which in FIG. 2 includes a break-open vial 27 with DMSO and a particle filter 41 for retaining the broken fragments. Another Y-shaped part 29, a connecting line segment 30, the Y-shaped part 23, and the connecting line 24 form a fluidic connection to the syringe 25, which is connected to the supply device 26 for DMSO via a connecting line 31 and can transfer DMSO to the freezer container 12 via the appropriate setting of the selector valve 32 by piston movement. A selector valve 32 is also provided in the fifth exemplary embodiment.

In FIGS. 3 and 4, the connection between the freezer container 12 and the supply device for DMSO is also effected via a connecting line 28 that leads to the syringe 25 with a selector valve 32. The connection 31 there leads to a vial 33 with DMSO that is punctured by means of a cannula (not shown in greater detail).

In FIG. 2, the top section 4 of the separation container 1 is connected to a removal device for removing blood plasma. The removal device is represented by the syringe 25, which is connected via connecting line 34, Y-shaped part 29, tube segment 30, Y-shaped part 23, connecting line 24, and selector valve 32 to the top section 4. The supply device 10 for HES, supply device 26 for DMSO, and the syringe 25, together with all connecting lines 28, 24, 31, HES line 22, connecting line segment 30, Y-shaped parts 23, 29, and tube clamps 35 for interrupting the fluidic connection, as well as the separation container 1 and the freezer container 12 and where applicable the supply device 42 for filler in FIG. 4 are components of a closed system. The system is closed after the separation container 1 has been filled with blood via the connecting line 18 and the connector 14.

The system is closed in that all of the components, the separation container 1, the syringe 25, the DMSO supply device 26, the supply device 10 for HES, the freezer container 12, if applicable the supply device 42 for filler (FIG. 4), if applicable the receptacle 49 for erythrocytes (FIG. 1), if applicable the pressure equalization device 39 (FIGS. 3 through 11) are arranged in a covering/enclosing container 45 and are sterilized.

The container 45 encloses a substance—such as blood, its components, HES—and also the syringe 25, the selector valve 32, the break-open vial 27, the particle filter 41, where applicable the vial 33 (FIGS. 3, 4). The connecting lines 28, 24, 31, the HES line 22, the connecting line segment 30 are connected in a sterile manner to one another and to the containers 45 for the syringe 25, the DMSO supply device 26, the supply container or supply device 10 for HES, the separation container 1, and the freezer container 12. The syringe 25, the selector valve 32, and the break-open vial 27, where applicable the vial 33 may be actuated from outside, without opening the container 45, that is, while maintaining the wall of the container 45. Support elements 37 for stabilizing the center section 3 are included in the container 45 that embodies the separation container 1. Excess air is released via the selector valve 32 for the syringe 25 into the bag-like container 45 enclosing the syringe 25. In FIG. 4, broken lines indicate clamping devices that can separate the sections 2, 3, 4 and the freezer container from one another, which is necessary in particular prior to the first centrifugation between freezer container 12 and top section 3 and which after the centrifugation is necessary for preventing undesired mixing at least between the bottom section 2 and the center section 3.

The syringe 25 in accordance with FIGS. 3 and 4 and in accordance with FIGS. 5 through 10 transports, pumps, and meters only DMSO, where necessary contained in a cryoprotective mixture. Covering containers 45 for all components are also provided there, so that closed components there inside a closed system also correspond to one another contamination free. In FIGS. 3 and 4, excess air is released via the selector valve 32 into a pressure equalization device 39. In the fifth exemplary embodiment, the selector valve 32 and the round filter 50 are not enclosed by a container 45, but are still sealed in a sterile manner from the environment.

The supply device 8 for blood does not offer many contact surfaces for interaction with the environment. Thus, in accordance with FIGS. 2, 5 the two supply devices 20 for anticoagulant are contained in containers 45 and connected in a sterile manner to the connecting line 18. The only weak points are the cannulas 15, which only briefly open the system when they perforate the latex covering, the system being closed up until the removal of the cord blood from the umbilical cord 16. A cannula protection unit 19 is pulled over the cannula 15 prior to and after its use to protect the medical technicians from injury.

FIGS. 5 through 12 depict a fifth exemplary embodiment that has both the inventive separation container 1 and a second example of the inventive system.

Figure 5:
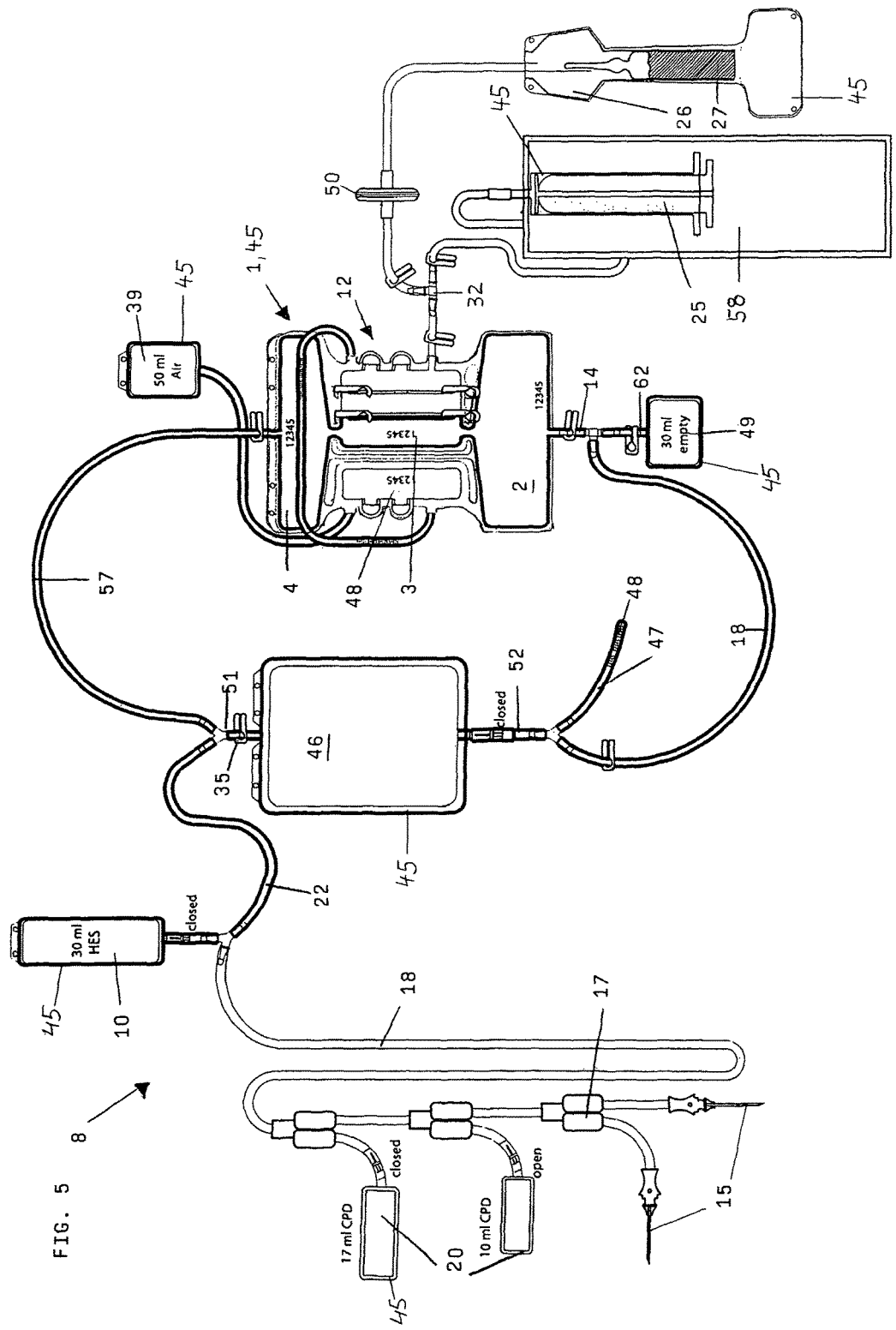
FIG. 5 is a diagram of an elevation of a second example of the inventive system having a supply device for blood, a separation container in accordance with a fifth exemplary embodiment, and other addition devices, wherein the freezer container may be embodied by the center section of the separation container—just prior to the blood being removed from the umbilical cord.

FIG. 5 depicts the system as it is just prior to removal of blood from the umbilical cord 16 (shown only in FIG. 2). As in FIG. 2, the system includes supplying the blood, subsequent centrifugation/fractioning, subsequent preparation of the buffy coat in the freezer container 12, and the step-wise elimination of all system components except for the freezer container 12. The supply device 8 for blood includes two cannulas 15 for removing blood from the umbilical cord (not shown), a supply device 10 for HES, a blood collection container 46, and a sampling section 47 with a patient-specific identification number 48.

Proceeding from a Y-shaped part 17, the cannulas 15 form the ends of a connecting line 18. Provided on the connecting line 18 are two additional Y-shaped parts 17, via which supply devices 20 for anticoagulant to prevent blood clots are connected to the connecting line 18. First 17 mL of anticoagulant are conducted from the top anticoagulant supply device 20 into the blood collection container 46. The supply occurs via the tube clamp 35 on the top connector 51 of the blood collection container 46. Then the umbilical cord 16 is punctured and the blood is supplied to the blood collection container 46. Transport is enabled by the pulsing, pump action of the blood, which can be supported in that the system is placed below the puncture point and thus the effect of gravity may be used. Once the blood collection container 46 is nearly completely full, a second addition of 10 mL anticoagulant is made from the bottom supply device 20, and this cleans the connecting line 18 so that all of the blood travels into the collection container 46 without any significant loss of umbilical cord blood. After the filling of the collection container 46 has concluded, the connecting line 18 is welded off in a sterile manner just in front of the supply device 10 for HES and thus the cannulas 15 and the anticoagulant supply devices 20 are eliminated. The system is now closed and is not opened again, even if additional system components are separated, until someone needs buffy coat 65 from the freezer container 12. The system, already somewhat reduced, is now transported from the hospital to the blood bank.

Figure 6:
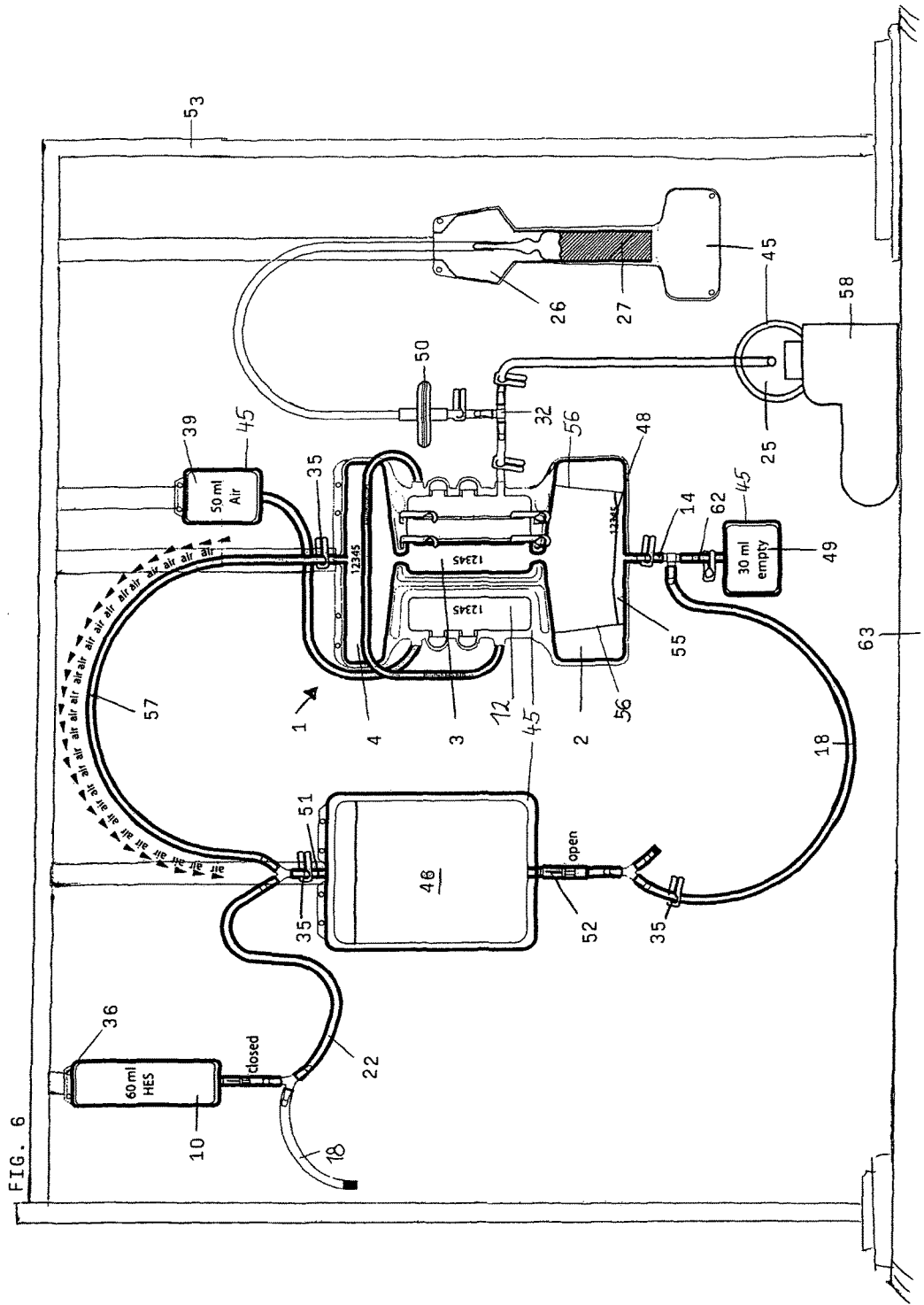
FIG. 6 is a diagram of an elevation of the system in accordance with FIG. 5, cannulas, anticoagulant supply devices, and sampling section already having been separated in a sterile manner and wherein the process of filling the separation container with blood from the blood collection container has begun.

In the blood bank, the system, with the exception of the syringe 25, is hung on fasteners 36 on the containers 45 in a stand 53, depicted in FIG. 6, and the connector 52 of the blood collection container 46 is opened in order to fill the sampling section 47 labeled with an identification number 48 with blood. For filling the sampling section 47 with blood, the former is rolled until empty or deaerated by means of a conventional roller tool towards the connector 52. This causes the sampling section 47 that has been rolled until empty to draw blood, until it is full, from the blood collection container 46. Thus sampling is conducted without opening the system. First the roller tool is used to remove air from a line. After the sampling section 47 has been filled with blood, the connector 52 is closed and the sampling section 47 is welded off in order to supply it with the blood to a centrifuge 54 depicted in FIG. 7 and to determine the hematocrit value, which is then used to draw conclusions about the packing volume and the space required in the bottom section 2 and its manipulation.

FIG. 6 depicts the inventive system at a time after which the volume has been manipulated on the bottom section 2. On the bottom section 2 only the volume between the welding seams 56 applied for manipulating the volume is provided for receiving erythrocytes 64 to be obtained for the upcoming centrifugation.

In FIG. 6 the separation container 1 has already begun to be filled with blood 55 starting from the blood collection container 46 and its open connector 52 and the connecting line, also labeled 18, via the bottom section 2 and the connector 14 there. The blood collection container 46 is emptied and filled with air, which comes from the separation container 1, via the top connector 51 that is opened to an air line 57. There is a quasi circulation, the air from the separation container 1 being displaced into the blood collection container 46 as the former is filled with blood. The air line 57 is connected to the top section 4 and is then closed by means of the tube clamp 35 when the blood coming from the blood collection container 46 via the connecting line 18 has risen to the upper edge of the top section 4. Arrows labeled "air" indicate the direction of the air flow in the air line 57.

It may be seen from FIG. 6 that in the fifth exemplary embodiment the syringe 25 may also be operated by means of the pump 58, which in particular plays a role in the addition of DMSO. In contrast, the syringe 25 is filled with DMSO manually. In addition, the separation container 1 at its sections 2, 3, 4 and the freezer container 12 are labeled with the identification number 48 and a pressure equalization device 39 for the freezer container 12 and a receptacle 49 for any excess erythrocytes 64 after centrifugation are available.

Once the separation container 1 is filled with blood 55, the air line 57 initially remains open and a fluidic connection is also established via the HES line 22 between the supply device 10 for HES and the blood collection container 46, which has now been emptied and which is still fluidically connected to the separation container 1. Thus, HES also travels via the blood collection container 46, the connecting line 18, and the connector 14 and bottom section 2 into the separation container 1, carrying all remaining valuable blood 55 with it. When supplying HES has concluded, the separation container 1 is closed via tube clamps 35. The system is reduced again in that the blood collection container 46 and thus also the supply device 10 for HES is welded off in a sterile manner at regions of the air line 57 and connecting line 18 that are close to the connectors.

Figure 7:
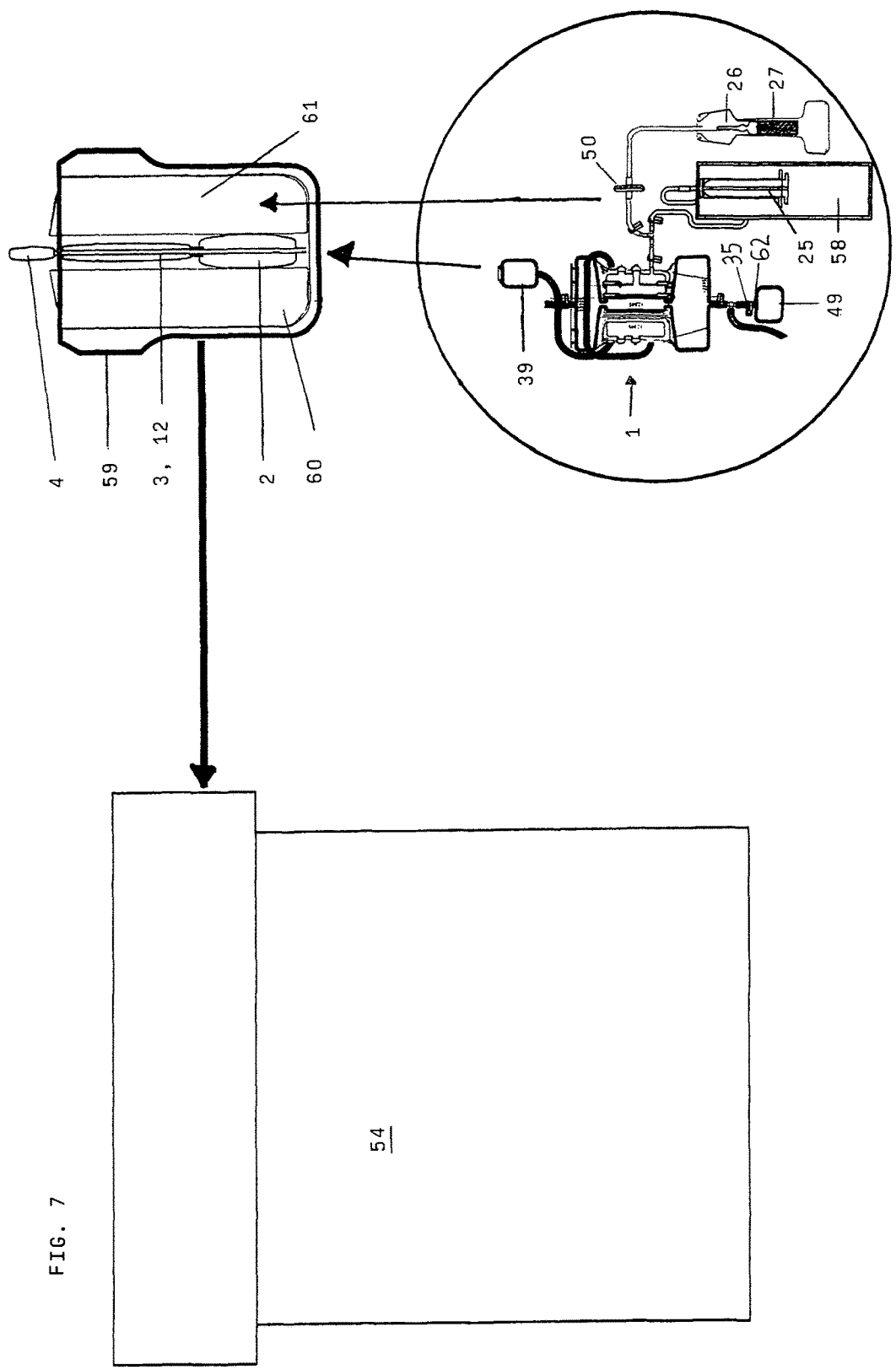
FIG. 7 is a diagram of an elevation of the system in accordance with FIG. 6, HES and blood collection containers already being separated in a sterile manner and the system being inserted into a centrifuge beaker.

FIG. 7 depicts that the remaining system is inserted into a centrifuge beaker 59. The centrifuge beaker 59 has two inner containers 60 and 61. The inner container 61 receives the covered syringe 25, the pump 58, and the supply device 26 for DMSO. The inner container 60 may be filled with filler (solid or liquid) to equalize the weight, to ensure balance, and then may be closed. The outer surfaces of the inner containers 60, 61 that face one another form a receiving unit that is largely adapted to the shape of the separation container 1 and also make it possible to accommodate the pressure equalization device 39 and the receptacle 49, the connector 62 of which is closed by a tube clamp 35 during centrifugation. The centrifuge beaker 59 is closed with a cover (not shown) such that the top section 4 is not damaged, either. Finally, the centrifuge beaker is placed into the centrifuge 54 and centrifuged.

Figure 8:
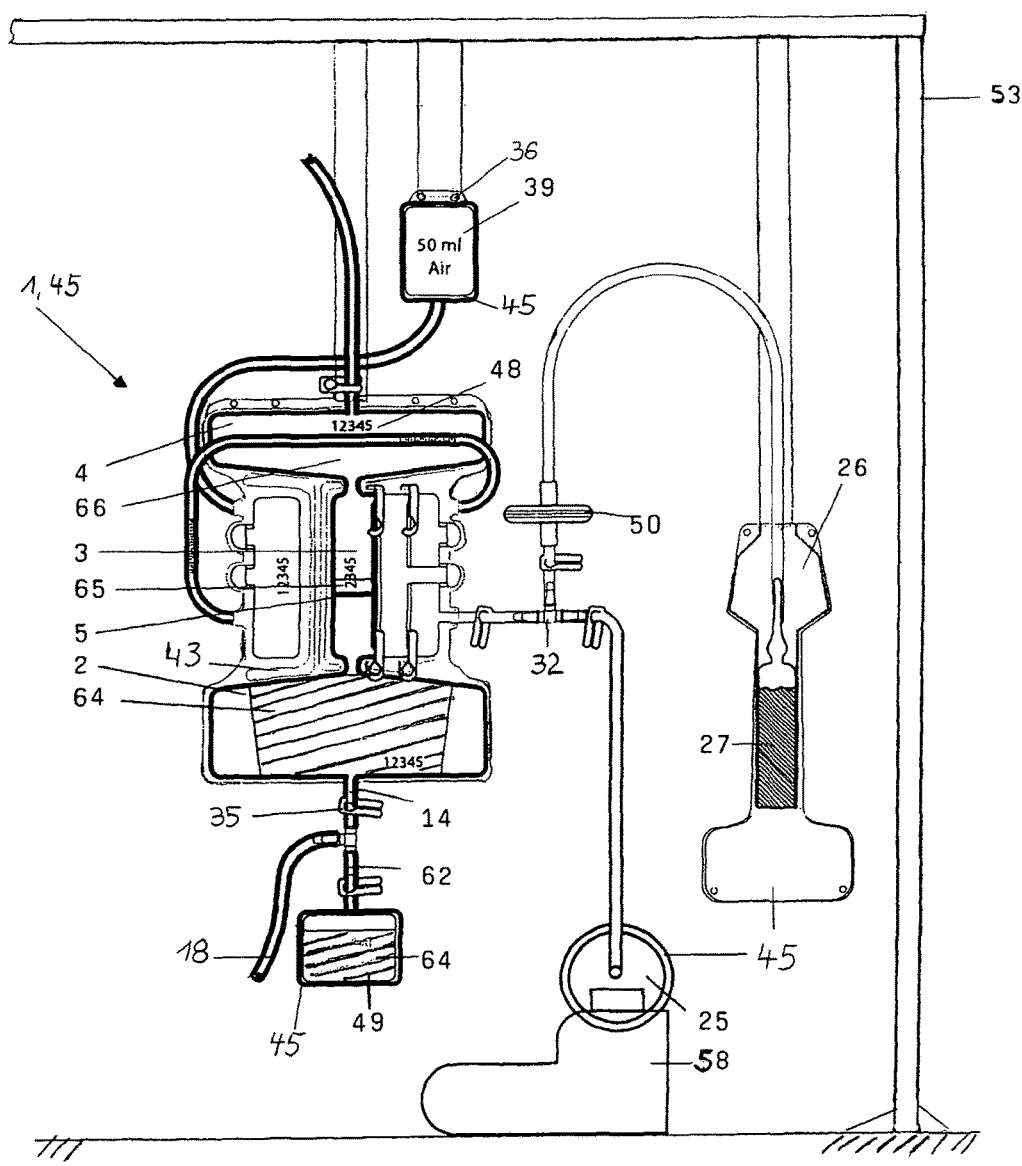
FIG. 8 is a diagram of an elevation of the system in accordance with FIG. 7, after centrifugation.

FIG. 8 depicts that after centrifugation the system is removed from the centrifuge 54 and is reattached to the stand 53 or placed the base 63. The phase boundary 5 extends transversely across the center section 3, the buffy coat 65 extends a little below the half of the center section 3 above the phase boundary 5, and the blood plasma 66 is thereabove. In and of itself, the region below the phase boundary 5 and the bottom section 2 was filled with erythrocytes 64, which here in FIG. 8 however have already been released via the bottom section 2 from the center section 3 into the receptacle 49 for erythrocytes 64 in order to keep the region of the freezer container 12 largely free of erythrocytes 64. In this case the capacity of the receptacle 49 is fixed at 30 mL and its capacity is generously matched to the expected quantity of erythrocytes 64, shown here with the hatch lines, from the center section 3. Thus, in FIG. 8 some of the erythrocytes 64 have been released into the receptacle 49 so that the erythrocytes 64 in the separation container 1 may only yet be found in the bottom section 2 and the freezer container 12 with the integrated center section 3 and the top section 4 with the blood plasma 66 may be supplied for additional work steps.

In a next step, the bottom section 2 labeled with an identification number 48 and the receptacle 49 are separated from the rest of the system in a sterile manner. The separation container 1 comprises a container 45 that was made from films disposed on top of one another and that has different chambers that may be connected to one another and may be separated from one another and also has blank fields 43. The blank fields 43 are made of connected, chamber-free film sections that are disposed directly on one another and that permit sections of the separation container 1 to be separated and welded off from one another in a simple and sterile manner. In any case, the connection of the center section 3 to the bottom section 2 is closed in a sterile manner without the system being opened.

Figure 9:
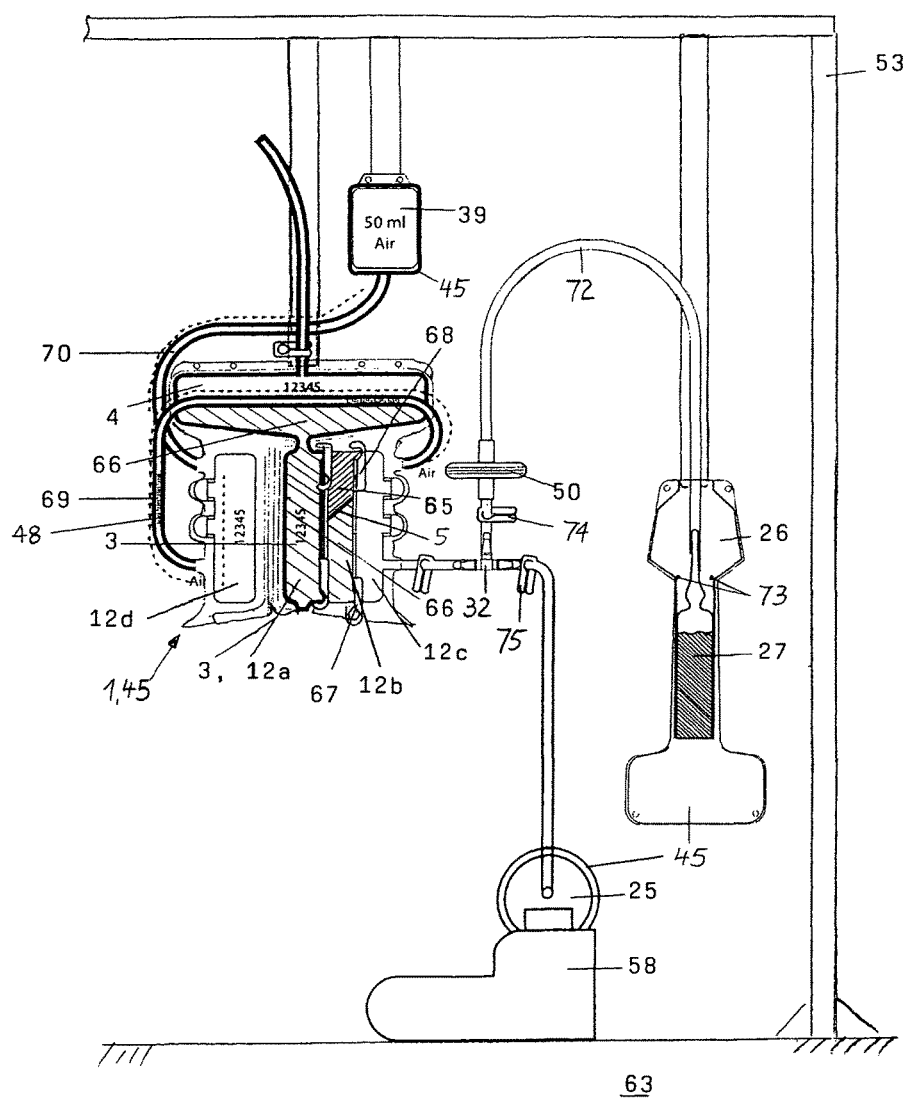
FIG. 9 is a diagram of an elevation of the system in accordance with FIG. 8, the bottom section being separated in a sterile manner and buffy coat flowing from the center section into another compartment of the freezer container.

FIG. 9 depicts that the bottom section 2 has been separated in a sterile manner and the buffy coat 65 has been transferred from the center section 3, which simultaneously forms the compartment 12a of the freezer container 12, to another compartment 12b of the freezer container 12. To this end, the bottom closure 67 between the compartments 12a and 12b is opened and the buffy coat 65 is displaced into the compartment 12b by the blood plasma 66 coming from the top section 4. The buffy coat 65 is indicated by hatch marks inclining upward to the right, and the blood plasma 66 is indicated by hatch marks inclining upward to the left. So that air that is also trapped therein does not create a problem, the closure 68 is opened slightly such that air can exit through the compartment 12c into the air line 69. In the present fifth exemplary embodiment, the connecting line 69, also labeled with the identification number 48, opens into the compartment 12d of the freezer container 12. From there the displaced air can enter via the air line 70 into the pressure equalization container 39, which has a specific capacity for the air displaced from the freezer container 12.

If the compartments 12a and 12b are completely filled with buffy coat 65 and blood plasma 66, the connection between the top section 4 and center section 3 or compartment 12a is closed, in this case it is welded closed, and the top section 4 is completely separated. Now buffy coat 65 and blood plasma 66 are mixed and distributed to compartments 12a, 12b, and 12c. The distribution may be performed manually. A shaker device 71 supports this. The connecting line 69 is closed.

Once the mixture of buffy coat 65 and blood plasma 66 has been distributed, which is illustrated in FIG. 10 by the cross-hatching in the compartments 12a, 12b, 12c, DMSO is added via the pump 58 and the syringe 25. First the syringe 25 is filled manually and actuated from outside through wall of the container 45 covering it by drawing the piston with DMSO from the break-open vial 27. The break-open vial 27 is broken open and displaced upward for drawing the syringe 25 initially inside the supply device 26 for DMSO so that the end of the DMSO line 72 reaches to the bottom of the break-open vial 27. Provided inside the supply device 26 for DMSO are shoulders 73 that are flexible but sufficiently stable to fix the break-open vial 27 that has been displaced upward. The tube clamps 74, 75 are removed and the syringe 25 draws the DMSO via the DMSO line 72 and the selector valve 32, which has been moved to the correct open position. A round filter 50 retains the fragments from the break-open vial 27. After this process, the supply device 26 for DMSO is separated from the rest of the system in a sterile manner. Care has also been taken here that the system is not opened and thus work may be performed in a normal laboratory rather than in an expensive cleanroom.

FIG. 10 depicts the rest of the system after the separation of the supply device 26 for DMSO. The figure shows that the DMSO travels from the syringe 25 and the pump 58 via the DMSO line 72 into the freezer container 12, in this case the compartment 12c. In the fifth exemplary embodiment, pure DMSO is not used, but rather it is used in a mixture of 50% DMSO and 50% of a 10% aqueous solution of "DEXTRAN 40". When filling the freezer container 12, the syringe 25 works with a pump 58 that ensures that the filling proceeds slowly and takes approx. 10 min.

FIG. 10 further depicts that DMSO, in this case in the mixture, initially travels into the compartment 12c. Air is displaced via the connecting line 69 to the compartment 12d and from there travels into the pressure equalization device 39. The freezer container 12 is arranged on a cooled shaker device 71 that ensures that DMSO spreads uniformly into all three compartments 12a, 12b, 12c.

FIG. 11 depicts that the DMSO line 72 that is still necessary in FIG. 10 has now been welded closed and removed. The system now still contains just the freezer container 12 with the connecting line 69, air line 70, and pressure equalization device 39, which is arranged on the stand 53. The freezer container 12 is arranged on the shaker device 71. A die 76 is placed onto the compartments 12a, 12b, and 12c and has on its bottom a shape that is matched to compartments 12a, 12b, 12c, but that is dimensioned such that some of the mixture of buffy coat 65, blood plasma 66, and DMSO is displaced to the connecting line 69 and into the compartment 12d, which is still empty. Pressure is exerted from above onto the compartments 12a, 12b, 12c and compartment 12d is filled. The displaced air travels via the air line 70 into the pressure equalization device 39.

Once the mixture of buffy coat 65, blood plasma 66, and DMSO has been distributed and the entire freezer container 12 is filled uniformly, the die 76 is removed and the air line 70 is welded off from the compartment. FIG. 12 also illustrates that the connecting line 69 is separated in a sterile manner and the ends are closed in a sterile manner. In addition, FIG. 12 illustrates that the freezer container 12 is divided into two parts. A first part includes the compartment 12d, and a second part includes the compartments 12a (center section 3), 12b, 12c. The two parts may now be stored in different blood banks and can always be tracked using the identification numbers 48. The buffy coat mixture may then be removed easily and contamination-free via the connectors (not shown in greater detail) that are covered in a sterile manner; each of the two parts has two of these. In FIGS. 7 and 8, the two connectors for the part that includes the compartments 12a, 12b, 12c are embodied such that one opens into the compartment 12b and one into the compartment 12c. The other connecting line 69 may be used for sampling.

Refer to the general section of the description for other features not illustrated in the figures. In particular, pressure equalization devices (not shown here) are also provided in the exemplary embodiments depicted in FIGS. 1 through 4, so that displaced air remains in the system and there is no interaction with the environment.

In closing, it should be noted that the inventive teaching is not limited to the exemplary embodiments explained in the foregoing.

The invention claimed is:

1. A method for separating blood, wherein different blood fractions, including erythrocytes, buffy coat, and blood plasma, are obtained, the method comprising:
    introducing blood into a separation container and performing a first centrifugation of the separation container such that the blood fractions of the blood collect in different, fluidically connected sections of the separation container arranged above one another, the separation container having a top section for receiving the blood plasma, a center section for receiving the buffy coat, and a bottom section for receiving the erythrocytes;
    wherein the future packing volume of the erythrocytes to be centrifuged is determined using the hematocrit value of the supplied blood,
    wherein the capacity of the bottom section is adapted to the expected packing volume of the erythrocytes after centrifugation such that the phase boundary forming between buffy coat and erythrocytes during centrifugation is positioned in a region of the center section of the separation container that is adjacent to the bottom section, the method further comprising:
    introducing the quantity of supplied blood into the separation container, wherein the quantity is based upon the expected packing volume of the erythrocytes,
    wherein a freezer container is fluidically connected to the separation container at the top section of the separation container,
    wherein the fluidic connection between the freezer container and the separation container is closed during the first centrifugation of the separation container and the freezer container, the method further comprising:
    separating the bottom section from the center section after the first centrifugation;
    opening the fluidic connection between the freezer container and the separation container after the first centrifugation and after the bottom section has been separated from the center section; and
    performing a second centrifugation in a direction opposite a direction of the first centrifugation after opening the fluidic connection between the freezer container and the separation container to cause the buffy coat to travel out of the center section of the separation container, through the top section of the separation container, and into the freezer container and to cause the blood plasma, which is lighter than the buffy coat, to travel to the center section.

2. The method in accordance with claim 1, wherein hydroxyethyl starch (HES) solution is added to the blood prior to centrifugation.

3. The method in accordance with claim 1, wherein the capacity of the freezer container is adapted to the visible quantity of buffy coat after centrifugation.

4. The method in accordance with claim 1, further comprising adding at least one of DMSO, blood plasma, or a mixture thereof to the freezing container.

5. The method in accordance with claim 4, wherein the capacity of the freezer container is adapted to the visible quantity of buffy coat after centrifugation, taking into account the addition of the at least one of DMSO, blood plasma, or a mixture thereof.

6. The method in accordance with claim 1, wherein the blood is introduced into the separation container via a sterile connector of the separation container, wherein additional substances are added to the separation container or to the freezer container via sterile connections, and wherein the separation container, the freezer container, and one or more other removal and/or supply devices having a reservoir and/or mixing and/or transport and/or metering function are connected to one another in a sterile manner, such that the separation container, the freezer container, and all other removal and/or supply devices having a reservoir and/or mixing and/or transport and/or metering function are in a closed system.

7. The method in accordance with claim 6, further comprising:
    connecting a supply device for blood to introduce the blood to the separation container; and
    disconnecting the supply device for blood in a sterile manner after the separation container has been filled and before centrifugation.

8. The method in accordance with claim 1, wherein a plurality of removal and/or supply devices having a reservoir and/or mixing and/or transport and/or metering function for at least one of DMSO, blood plasma, and HES; a pressure equalization device; or a receptacle for erythrocytes are added with the separation container together to a centrifuge beaker and after centrifugation the removal and/or supply devices are gradually removed until the freezer container is left.

9. The method in accordance with claim 8, wherein the freezer container comprises at least two compartments.

10. A separation container for a blood centrifuge having a bottom section for receiving erythrocytes, having a center section for receiving buffy coat, and having a top section for receiving blood plasma, wherein the center section has a smaller cross-sectional dimension than the top and bottom sections, wherein the sections are fluidically connected and wherein the bottom section is separable from the center section, wherein the capacity of the bottom section is adaptable to the expected packing volume of the erythrocytes after a first centrifugation such that the expected packing volume is completely accommodated by the bottom section and such that a phase boundary between erythrocytes and buffy coat is positioned in a region of the center section that is adjacent to the bottom section, wherein the separation container is fluidically connectable to a freezer container at the top section of the separation container, wherein the separation container and the freezer container are configured to be disconnected during the first centrifugation of the separation container and the freezer container, wherein the separation container and the freezer container are configured to be fluidically connected during a second centrifugation in a direction opposite to a direction of the first centrifugation, wherein the freezer container is connected in a sterile manner to a supply device for dimethyl sulfoxide (DMSO) and to a syringe, wherein the syringe fulfills transport, storage, and/or mixing functions, wherein the separation container, the freezer container, the supply device for DMSO, and the syringe are components of a closed system, wherein the individual components are included inside containers that are sterile coverings and do not permit any interaction with the environment, and wherein the individual components are connected in a sterile manner and are configured to be separated in a sterile manner.

11. The separation container in accordance with claim 10, wherein the separation container has a receptacle for erythrocytes that is connected in a sterile manner to a connector and may be separated therefrom, in a sterile manner, after centrifugation and after receiving erythrocytes.

12. The separation container in accordance with claim 10, wherein the capacity of the freezer container may be adapted to the expected yield of centrifuged buffy coat from the center section and where necessary to the addition of at least one additional substance.

13. The separation container in accordance with claim 10, wherein the separation container prior to centrifuging is connected to a supply device for supplying the blood, in a sterile manner via a connector, wherein after the separation container has been filled with blood and before centrifugation, the supply device for blood is separable therefrom in a sterile manner.

14. The separation container in accordance with claim 13, wherein the separation container is connected to a supply device for HES in a sterile manner via a connector, wherein after the separation container has been filled with HES the supply device for HES may be separated therefrom in a sterile manner.

15. The separation container in accordance with claim 10, wherein the separation container includes a pressure equalization device for air or inert gas.

16. The separation container in accordance with claim 10, wherein the supply device for DMSO includes a blood collection container that is configured to function as a pressure equalization device as necessary, and wherein a supply device for HES is connected to the blood collection container in a sterile manner, wherein after the separation container has been filled with HES via the blood collection container the supply device for HES may be separated from the latter in a sterile manner.

17. The separation container in accordance with claim 10, wherein a filter is provided between the supply device for DMSO and the syringe.

18. The separation container in accordance with claim 16, wherein the supply device for HES and, where necessary, a blood collection container of a supply device for blood, are components of a closed system, wherein the individual components are included inside of containers that act like sterile coverings and do not permit any interaction with the environment, and wherein the individual components are connected in a sterile manner and may be separated in a sterile manner.

19. The separation container in accordance with claim 10, wherein at least one identification number is applied to the bottom, center, and top sections of the separation container, and where necessary to a sampling section connected to the separation container.

20. The separation container in accordance with claim 10, wherein the fill volume of the separation container is up to approximately 500 mL.

* * * * *

UNITED STATES PATENT AND TRADEMARK OFFICE
CERTIFICATE OF CORRECTION

PATENT NO. : 10,350,340 B2  
APPLICATION NO. : 14/127817  
DATED : July 16, 2019  
INVENTOR(S) : Pobitschka Page 1 of 1

It is certified that error appears in the above-identified patent and that said Letters Patent is hereby corrected as shown below:

On the Title Page

Item (87) PCT Pub. No.: "WO2017/175069" should read --WO2012/175069--.

Signed and Sealed this  
Seventeenth Day of March, 2020

Andrei Iancu  
*Director of the United States Patent and Trademark Office*